(12) United States Patent
Smith, III et al.

(10) Patent No.: US 7,772,159 B2
(45) Date of Patent: *Aug. 10, 2010

(54) SOLUTION AND SOLID PHASE SYNTHESIS OF PYRROLINONES AND POLYPYRROLINONES

(75) Inventors: Amos B. Smith, III, Merion, PA (US); Hu Liu, Quincy, MA (US); Hiroyuki Ikumura, Osaka (JP); Ralph F. Hirschmann, Pasedena, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/894,916

(22) Filed: Jul. 20, 2004

(65) Prior Publication Data

US 2005/0004371 A1 Jan. 6, 2005

Related U.S. Application Data

(62) Division of application No. 09/841,951, filed on Apr. 25, 2001, now Pat. No. 6,891,046.

(60) Provisional application No. 60/200,022, filed on Apr. 26, 2000.

(51) Int. Cl.
*C40B 50/14* (2006.01)
*C40B 50/18* (2006.01)

(52) U.S. Cl. .......................... 506/30; 506/32; 548/519; 514/422

(58) Field of Classification Search ........................ None
See application file for complete search history.

(56) References Cited

U.S. PATENT DOCUMENTS

| 5,514,814 A | 5/1996 | Hirschmann et al. |
| 5,770,732 A | 6/1998 | Hirschmann et al. |
| 6,034,247 A | 3/2000 | Smith, III et al. |

OTHER PUBLICATIONS

Smith, A. B.; Liu, H.; Okumura, H.; Favor, D. A.; Hirschmann, R. "Synthesis of Polypyrrolinones on Solid Support" Organic Letters Jun. 9, 2000, 2(14), 2041-2044.*
Smith et al. "Molecular Modeling, Synthesis, and Structures of N-Methylated 3,5-Linked Pyrrolin-4-ones Toward the Creation of a Privileged Nonpeptide Scaffold" Bioorganic & Medicinal Chemistry 1999, 7, 9-22.*
Wikipedia, the Free Encyclopedia. Valeric acid. Retrieved from http://en.wikipedia.org/wiki/Valeric_acid on Jan. 29, 2008, p. 1.*
eMolecules, Delta-Valerolactone. Retrieved from http://www.emolecules.com/cgi-bin/more?vid=503745 on Jan. 29, 2008, p. 1.*
eMolecules, Gamma-Valerolactone. Retrieved from http://www.emolecules.com/cgi-bin/more?vid=533176 on Jan. 29, 2008, p. 1.*
Hess, D.B., et al.; Readily Accessible 12-1-5(superscript 1) Oxidant for the Conversion of Primary and Secondary Alcohols to Aldehydes and Ketones; J. Org. Chem.; 1983; 48; 4155-4156.

Ireland, Robert E., et al.; An Improved Procedure for the Preparation of the Dess-Martin Periodinane; J. Org. Chem.; 1993; 58; 2899.
Look, Gary C., et al.; Trimethylorthoformate: A Mild and Effective Dehydrating Reagent for Solution and Solid Phase Imine Formation; Tetrahedron Letters, vol. 36; No. 17; pp. 2937-2940; 1995.
Smith, Amos B., et al.; Design and Synthesis of a Competent Pyrrolinone-Peptide Hybrid Ligand for the Class II Major Histocompatibility Complex Protein HLA-DR1; J. Am. Chem. Soc.; 1999; 121; 9286-9298.
Thompson, Wayne J., et al.; Synthesis and Antiviral Activity of a Series of HIV-1 Protease Inhibitors with Functionality Tethered to the P(subscript 1) or P(subscript 1 accent) Phenyl Substituents: X-ray Crystal Structure Assisted Design; J. Med. Chem.; 1992; 35; 1685-1701.
Smith, Amos B., III, et al.; Design, Synthesis and Evaluation of a Pyrolinone-Peptide Hybrid Ligand for the Class II MHC protein HLA-DR1; J. Am. Chem. Soc.; 1998; 120; 12704-12705.
Smith, Amos B., III, et al.; An Orally Bioavailable Pyrrolinone Inhibitor of HIV-1 Protease: Computational Analysis and X-ray Crystal Structure of the Enzyme Complex; J. Med. Chem. Soc.; 1997; 40; 2440-2444.
Smith, Amos B., III, et al.; Design and Synthesis of Peptidomimetic Inhibitors of HIV-1 Protease and Renin. Evidence for Improved Transport; Journal of Medicinal Chemistry; 1994;vol. 37; No. 2; 215-218.
Smith, Amos B., III, et al.; Molecular Modeling, Synthesis and Structures of N-Methylated 3,5-Linked Pyrrolin-4-ones Toward the Creation of a Privileged Nonpeptide Scaffold; Bioorganic & Medicinal Chemistry 7; 1999; 9-22.
Smith, Amos B., III, et al.; De Novo Design, Synthesis and X-ray Crystal Structures of Pyrrolinone-Based B-Strand Peptidomimetics; J. Am. Chem. Soc.; vol. 116; No. 22; 1994; pp. 9947-9962.
Smith, Amos B., III, et al.; Design, Synthesis and Crystal Structure of a Pyrrolinone-Based Peptidomemetic Possessing the Conformation of a B-Strand: Potential Application to the Design of Novel Inhibitors of Proteolytic Enzymes; J. Am. Chem. Soc.; vol. 114; No. 26; 1992; pp. 10672-10674.
DeWitt, Shelia H., et al.; Combinatorial Organic Synthesis Using Parke-Davis's Diversomer Method; Acc. Chem. Res.; 1996; 29; 114-122.

(Continued)

*Primary Examiner*—Christopher Low
*Assistant Examiner*—Christopher M Gross
(74) *Attorney, Agent, or Firm*—Porzio, Bromberg & Newman, P.C.

(57) ABSTRACT

The invention provides a new process for the preparation of polypyrrolinones (I) of various sizes which have found to be useful peptidomimetics. One aspect of the invention is a new process utilizing α-amino-α-substituted-valerolactones as synthons. A second aspect of the invention is a process for the synthesis of polypyrrolinones using solid-phase techniques.

(I)

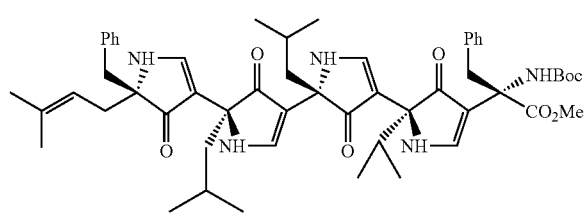

11 Claims, 6 Drawing Sheets

OTHER PUBLICATIONS

Thompson, et al.; Synthesis and Applications of Small Molecule Libraries; Chem. Rev. 1996; 96; 555-600.

Fruchtel, Jorg S., et al.; Organic Chemistry on Solid Supports; Angew. Chem. Int. Ed. Engl.; 1996; 35; 17-42.

Atherton, E. et al.; Solid Phase Synthesis, a Practical Approach; 1989; pp. 14-23.

Obrecht, D., et al.; Solid-Supported Combinatorial and Parallel Synthesis of Small-Molecular-Weight Compound Libraries; 1998; pp. 85-101.

Smith, A.B., Liu, H., Hirschmann, R.; A Second-Generation Synthesis of Polypyrrolinone Nonpeptidomimetics: Prelude to the Synthesis of Polypyrrolinones on Solid Support; Organic Letters 2000; 2; 14; 2037-2040.

Gung, B.W., Francis, M.B.; Diastereofacial Selectivity in Intramolecular 1,4-Conjugate Additions: Conclusive Evidence for the Importance of Ground-State Conformations and the o* Orbital Effect; J. Org. Chem.; 1993; 58; 6177-6179.

Carey, F.A. and Sundberg, R.; J. Advanced Organic Chemistry; Third Edition; Part B; 1990; Plenum Press; 1990; pp. 620-621.

* cited by examiner (a) (-)-7b, (MeO)₃CH/THF, 2 treatments; (b) KHDMS/18-c-6; (c) DMSO, (COCl)₂, DBU; (d) 31, (MeO)₃CH/THF, 2 treatments; (e) KHMDS; (f) CsF/DMF, TBAF; (g) PhCH₂CH₂CHO, (MeO)₃CH/THF, 2 treatments

SOLUTION AND SOLID PHASE SYNTHESIS OF PYRROLINONES AND POLYPYRROLINONES

CROSS REFERENCE TO RELATED APPLICATION

This application is a divisional patent application under 35 U.S.C. §120 of U.S. patent application Ser. No. 09/841,951, entitled New Solution And Solid Phase Synthesis of Pyrrolinones And Polypyrrolines filed Apr. 25, 2001, which is now U.S. Pat. No. 6,891,046, which issued May 10, 2005, which claims the benefit under 35 U.S.C. §119(e) of U. S. Provisional Application Ser. No. 60/200,022, entitled Process For The Synthesis of Polypyrrolinones on Solid Support, filed Apr. 26, 2000, the entirety of which is hereby incorporated by reference into this application.

GOVERNMENT SUPPORT

This invention was supported in part by funding from the U.S. Government (NIH Grant AI-42010-01-03) and the U.S. Government may therefore have certain rights in the invention.

FIELD OF THE INVENTION

The invention relates to a new process to prepare monomeric and oligomeric pyrrolinone peptidomimetic compounds utilizing α-substituted-α-aminovalerolactones as synthons and the adaptation of that process to solid phase synthesis.

BACKGROUND OF THE INVENTION

Compounds having biological activity can be identified by screening diverse collections (or libraries) of compounds that are produced by organic synthesis, fermentation or molecular biological methodologies. Drug discovery and optimization rely heavily on structure-activity relationships developed by altering the structure of lead compounds and determining the effect of these alterations on the observed biological activity. Complex molecules may require many structural modifications to understand the essential molecular architecture for optimum biological activity and techniques that can be used to accelerate the process are very valuable.

Combinatorial chemistry and compound libraries are valuable tools for both lead discovery and optimization and new methodology to prepare chemical libraries is a continuing need. Combinatorial libraries can be designed to maximize structural diversity or they can be designed to systematically vary substitution around a common chemical core. Because many ligands for biologically important receptors or enzyme active sites are non-peptides there is a continuing need to develop new techniques which will produce greater diversity and useful properties in more conventional small molecule libraries.

A variety of approaches to the preparation of chemical libraries have been developed. Many early efforts focused on using a limited set of high-yielding reactions thereby minimizing by-products and the need for purification steps. Alternatively, multi-component condensation reactions, e.g. the Ugi Reaction, can be exploited to assemble multiple fragments in a single reaction. While these approaches remain useful they fail to exploit many useful reactions which have been developed by synthetic organic chemists.

Syntheses of molecules on a solid support frequently facilitate both the synthesis and purification of chemical libraries. Solid phase synthesis was developed initially for peptide synthesis, and subsequently adapted to oligonucleotides. The range in molecular diversity in these natural biopolymers is relatively limited and the successful implementation of solid phase synthesis required optimization of a limited number of transformations. Small molecule libraries, however, exhibit a vastly greater range a complexity, structural diversity, and chemical reactivity and adaptation of solid-phase synthesis techniques to small molecules requires a significantly larger repertoire of synthetic methodology to efficiently access the diversity inherent in these small molecules. (Thompson, L. A. et al., *Chem. Rev.* (1996) 96:555; Fruchtel, J. S. et al., *Angew. Chem., Int. Ed. Engl.*, (1996) 35:17; Czarnik, A. W. and Ellman, J. A. (Eds.) *Combinatorial Chemistry Special Issue. Acc. Chem. Res.*, (1996) 29:112)

In solid phase synthesis a first reactant is attached to a solid support. This attachment can be a direct covalent bond to a functional group on the solid support or, alternatively, the attachment can be through molecular spacers or linkers between the solid support and the first reactant. Those spacers can be designed to modify the chemical reactivity of the reactant or to provide routes to ultimately cleave the compound from the solid support. As chemical reactions take place, the intermediate remains linked to the solid support while unreacted reagents or molecules can be removed easily by washing and filtration after each reaction step is completed. This allows large excess of reactants to be used to drive a reaction to a desired product without introducing serious purification problems. Immobilization of the reactant on a solid support produces high-dilution conditions which can promote intramolecular reactions and limit undesired side reactions. These relatively simple manipulations are readily automated which further increases the efficiency of the process. The added cost of the solid support is frequently offset by less labor-intensive purification steps and less need for solvents and adsorbents for chromatography. Multi-step processes can be carried out to efficiently produce complex organic molecules with minimal purification.

Peptides and proteins play a critical role in regulating many biological processes. Unfortunately peptides are susceptible to chemical and enzymatic hydrolysis and are difficult to deliver systemically. This has stimulated the search for biologically active small molecules, peptidomimetics, that mimic endogenous peptides, but are stable to physiologic conditions and are bioavailable after oral administration. Although a variety of scaffolds have been identified which mimic secondary conformations of proteins and polypeptides, the enormous variety of conformations found in nature affords a continuing need to identify useful templates to mimic polypeptides.

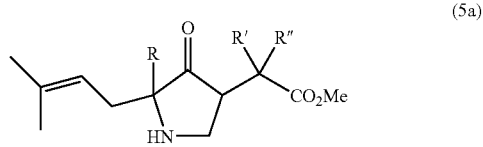

(5a)

-continued

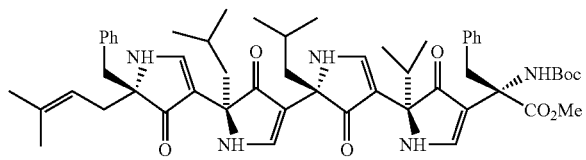
(21)

The 3,5,5-trisubstituted pyrrolin-4-one ring system, (5a) has proven to be a versatile template for the design of non-peptide peptidomimetics and polypyrrolinones (21) have been shown to be effective surrogates for polypeptides. Depending on their structure, polypyrrolinones, which are stable to both strong acid and proteases, can adopt diverse conformations including those analogous to β-strands (Smith, A. B., III et al., *J. Am. Chem. Soc.* 1992, 114, 10672; Smith, A. B., III et al., *J. Am. Chem. Soc.* 1994, 116, 9947), β-turns and helices (Smith, A. B., III et al., *Bioorg. Med. Chem.* 1999, 9). The β-strand structural motif was successfully utilized in the design and synthesis of several potent, bioavailable inhibitors of the HIV-1 aspartic acid protease which exhibited improved membrane transport properties relative to their peptidal counterparts. (Smith, A. B., III et al., *J. Med. Chem.* 1994, 37, 215; Smith, A. B., III, et al., *J. Am. Chem. Soc.* 1995, 117, 11113; Smith, A. B., III et al., *J. Med. Chem.* 1997, 40, 2440; Thompson, W. J., et al., *J. Med. Chem.* 1992, 35, 1685.) The improved transport was attributed to the presence of intramolecular hydrogen bonds between adjacent pyrrolinone rings (NH and CO), which led to a reduction in desolvation energy upon membrane transport (Hirschmann, R., et al. *In New Perspectives in Drug Design*; Dean, P. M., Jolles, G., Newton, C. G., Eds.; Academic: London, 1995; pp 1-14.). A bis-pyrrolinone was successfully used in the construction of a pyrrolinone-peptide hybrid ligand, which bound the Class II MHC protein HLA-DR1 in an extended β-strand-like conformation with similar potency to the native peptide. (Smith, A. B., III, et al. *J. Am. Chem. Soc.* 1998, 120, 12704; Smith, A. B., III; et al. *J. Am. Chem. Soc.* 1999, 121, 9286.)

Recent observations suggest that the polypyrrolinone structural motif, designed initially to mimic peptide and protein β-strand/β-sheet structural motifs may in fact represent a privileged nonpeptide scaffold, able to mimic not only the extended β-strand/β-sheet conformation, but also other diverse conformations including those analogous to β-turn and helices. This unexpected diversity, if accessible in controlled fashion, would expand the scope of the polypyrrolinone scaffold for the development of low-molecular weight ligands for a variety of biologically important targets.

An iterative solution phase syntheses of polypyrrolinones has been developed (FIG. 1) based upon the intramolecular cyclization of a metalloenamine derived from an α-amino acid derivative. Condensation of a latent 4-oxo-2-aminobutyrate derivative (1) with an aldehyde (2) produces the key imine (3). Deprotonation of (3) with KHMDS and subsequent intramolecular cyclization upon stirring the resulting potassium salt (4) at room temperature produces the 3,5,5-trisubstituted pyrrolinone (5). The olefinic (5a) or acetal (5b) side chains can be oxidatively or hydrolytically transformed to a new aldehyde (5c) which can be subjected to further iterations of the same reaction sequence to produce polypyrrolinones (6) (Smith, A. B., III, et al., *J. Am. Chem. Soc.* 1992, 114, 10672; *J. Am. Chem. Soc.* 1994, 116, 9947; *J. Am. Chem. Soc.* 1999, 121, 9286; U.S. Pat. No. 5,514,814; U.S. Pat. No. 5,770,732; U.S. Pat. No. 6,034,247; all incorporated herein by reference in there entirety). While this synthetic scheme is adequate to prepare limited numbers of analogs using conventional solution phase techniques, it is not well suited for the rapid preparation of large numbers of polypyrrolinones required for a pyrrolinone library. An iterative, solid-phase synthetic strategy is ideal to automate this multistep sequence.

The existing methodology (FIG. 1) required either a two-step oxidation [(a) OsO$_4$/NMO (b) NaIO$_4$; Approach A] or strong acid hydrolysis [Approach B] to unmask the aldehyde moiety at the outset of each successive synthetic cycle. It has now been found that the solid support is incompatible with a repetitive osmium catalyzed hydroxylation/oxidation process. While a single treatment was successful, subsequent hydroxylations failed. Moreover, ozonolysis, an alternative oxidative procedure is poorly adapted for automated synthesis. Acid hydrolysis of the acetal required increasingly strenuous conditions during each iteration of the cyclization process resulting in unacceptable degradation in yield and product purity. Thus it is apparent that further improvement in existing methodology is need to produce chemical libraries of these valuable compounds utilizing solid phase synthesis techniques.

BRIEF DESCRIPTION OF THE FIGURES

The numerous objects and advantages of the present invention can be better understood by those skilled in the art by reference to the accompanying figures, in which.

DETAILED DESCIPTION OF THE INVENTION

Figure 1:
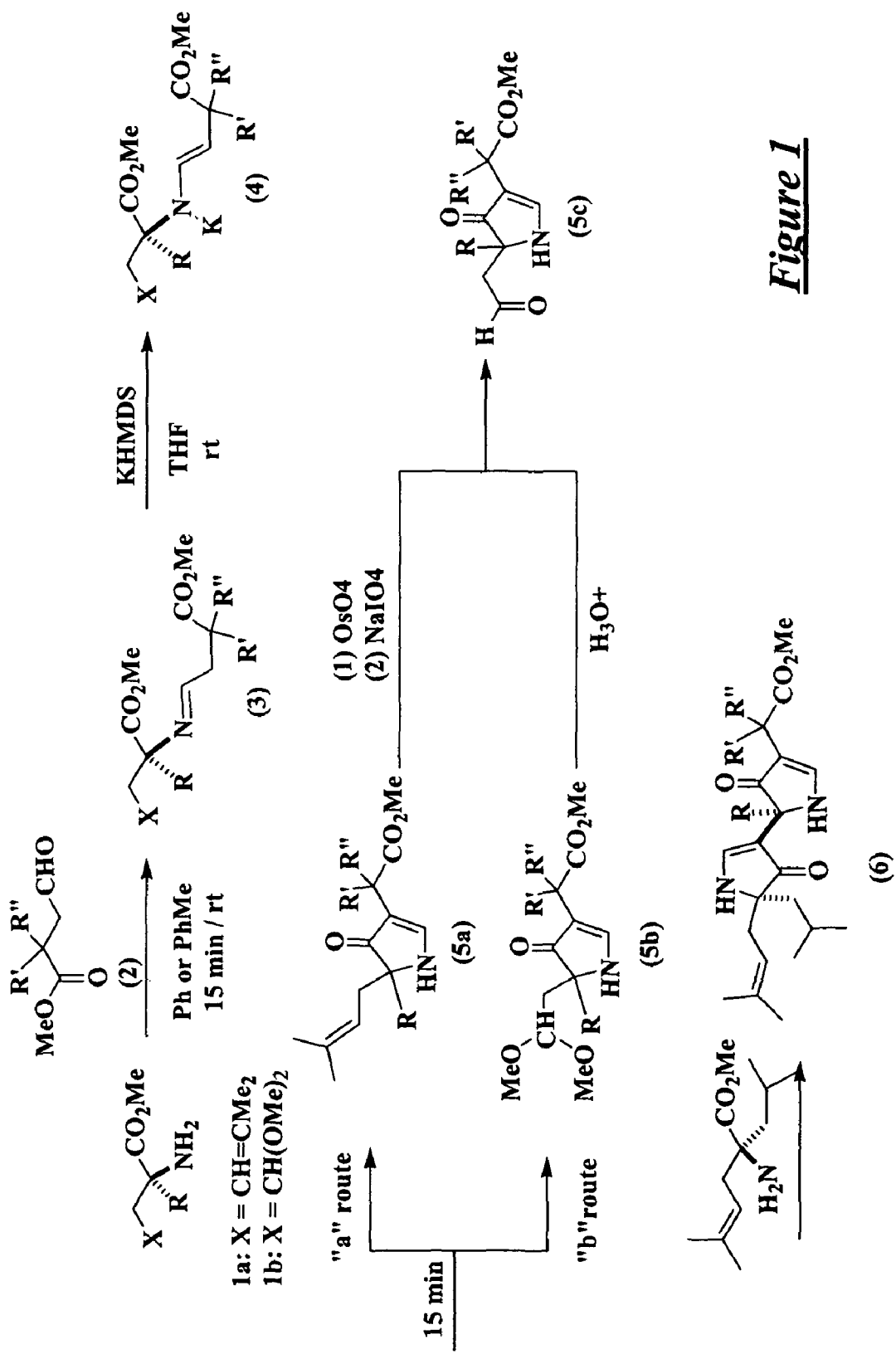
FIG. 1 shows a representative solution phase synthesis of linked pyrrolinones.

The following abbreviations and terms have been utilized throughout this document:
18-c-6-18 crown 6
Boc—tert-butoxycarbonyl
CI—chemical ionization
Cbz—Carbobenzyloxycarbonyl
DBU—Diazabicycloundecane
DVB—divinylbenzene.
DMSO—Dimethylsulfoxide
ES—electrospray
KHMDS—potassium hexamethyldisilazane
NMO—N-methylmorpholine-N-oxide
Pyr—Pyridine
rt—room temperature
Teoc—Trimethylsilylethoxycarbonyl
TBAF—tetrabutylammonium fluoride The term "protecting group" as used herein refers a chemical group that exhibits the following characteristics: (1) reacts selectively with the desired functionality in good yield to give the protected substrate wherein the protected functionality is stable to the projected reactions for which protection is desired; (2) is selectively removable from the protected substrate in high yields to reintroduce the desired functionality by reagents compatible with other functional groups encountered in such a reaction. Suitable protecting groups include acid-labile, base-labile, fluoride-labile, photolabile or removeable under neutral conditions. See, e.g. Wuts and Greene, Protecting Groups in Organic Synthesis, Wiley, 1999 which is incorporated herein by reference. The choice of a protecting group will be determined generally by the reaction conditions encountered and the other protecting groups which may be present in the molecule and examples of protecting groups with particular utility herein include alkoxycarbonyl amino protecting groups, e,g, tert-butoxycarbonyl, benzyloxycarbonyl, fluorenylmethoxy-carbonyl, trimethylsilylethoxycarbonyl and the acetal protecting groups for aldehydes. The term "latent" as used herein is meant to refer to an inert function group which can be selectively converted to the another functional group at the appropriate point in the synthetic sequence. Examples of "latent" aldehydes are the 3-methyl-but-2-enyl or 2-hydroxyethyl side chain which can be converted to an aldehyde using a variety of oxidative conditions.

The term "amino acid" is used herein refers to naturally occurring amino acids, as well as to optical isomers (enantiomers and diastereomers), synthetic analogs and derivatives thereof. α-Amino acids comprise a carbon atom bonded to a carboxyl group, an amino group, a hydrogen atom and a unique "side chain" group. The side chains of naturally occurring amino acids are well known and include hydrogen, alkyl, hydroxyalkyl, thioalkyl, alkylthioalkyl, branched alkyl, carboxyalkyl, carboxamidoalkyl, aminoalkyl, arylalkyl, and heteroarylalkyl moieties. The term "amino acid" also refers to α-substituted amino acids which comprise a carbon atom bonded to a carboxy group, an amino group and two unique "side chain" groups.

The term "alkyl group" as used herein means a saturated, monovalent, unbranched or branched hydrocarbon chain. Examples of alkyl groups include, but are not limited to, $C_1$-$C_8$ alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. An alkyl group can be unsubstituted or substituted with one or two suitable substituents.

The term "cycloalkyl group" as used herein means a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, $C_3$-$C_7$ cycloalkyl groups, such as cyclopropyl, cyclobutyl, cyclopentyl, cyclohexyl, and cycloheptyl, and saturated cyclic and bicyclic terpenes and $C_3$-$C_1$ cycloalkenyl groups, such as cyclopropenyl, cyclobutenyl, cyclopentenyl, cyclohexenyl, and cycloheptenyl. A cycloalkyl group can be unsubstituted or substituted by one or two suitable substituents. Preferably, the cycloalkyl group is a monocyclic ring or bicyclic ring.

The term "alkenyl group" as used herein means a monovalent, unbranched or branched hydrocarbon chain having one or more double bonds therein. The double bond of an alkenyl group can be unconjugated or conjugated to another unsaturated group. Suitable alkenyl groups include, but are not limited to $C_2$-$C_8$ alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)- pentenyl. An alkenyl group can be unsubstituted or substituted with one or two suitable substituents.

The term "aryl group" as used herein means a monocyclic or polycyclic-aromatic group comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more suitable substituents. Preferably, the aryl group, is a monocyclic ring, wherein the ring comprises 6 carbon atoms, referred to herein as "$C_6$ aryl".

A "heteroaryl group" means a monocyclic- or polycyclic aromatic ring comprising 15 carbon atoms, hydrogen atoms, and one or more heteroatoms, preferably, 1 to 3 heteroatoms, independently selected from nitrogen, oxygen, and sulfur. For the purposes of the invention, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, phienyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3-heteroatoms, referred to herein as "$C_2$-$C_5$ heteroaryl".

The term "alkoxy group" as used herein means an —O-alkyl group, wherein alkyl is as defined above. An alkoxy group can be unsubstituted or substituted with one or two suitable substituents. Preferably, the alkyl chain of an alkyloxy group is from 1 to 8 carbon atoms in length, referred to herein as "$C_1$-$C_8$ alkoxy".

The term "benzyl" as used herein means $CH_2$-phenyl. A benzyl group can be unsubstituted or substituted with one or more suitable substituents.

The term "phenyl" means $C_6H_5$. A phenyl group can be unsubstituted or substituted with one or more suitable substituents.

The term "carbonyl" group as used herein means a divalent group of the formula —C(O)—.

The term "alkoxycarbonyl" group as sued herein means a monovalent group of the formula C(O)-alkoxy. Preferably, the hydrocarbon chain of an alkoxycarbonyl group is from 1 to 8 carbon atoms in length, referred to herein as a "lower alkoxycarbonyl" group.

The term "halogen" as used herein means fluorine, chlorine, bromine, or iodine. Correspondingly, the meaning of the term "halo" encompass fluoro, chloro, bromo, and iodo.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

The term "clathrate" as used herein means a compound of the invention or a salt thereof in the form of a crystal lattice that contains spaces (e,g., channels) that have a guest molecule (e,g., a solvent or water) trapped within.

The term "optical isomer" or "diastereomer" as used herein refers to molecules containing one or more asymmetric centers and may therefore give rise to enantiomers, diastereomers and other stereoisomeric forms that are defined in terms of absolute stereochemistry as (R)- or (S)-, or as (D)- or (L)- for amino acids. The present invention is meant to include all such possible diastereomers, as well as their racemic and optically pure forms. Where the compounds described contain double bonds or other centers of geometric asymmetry, and unless specified otherwise, it is intended to include both (E)- and (Z)- isomers. Likewise all tautomers are intended to be included.

The term "chemical library" or "array" as used herein means a designed collection or differing molecules which can be prepared by chemical or biotechnological means and which can be screened for biological activity in a variety of different formats (e.g. soluble molecules and molecules linked to a sold support).

The term "solid support" as used herein refers to an insoluble substance with appropriate sites to link organic molecules during the synthetic steps. Solid supports may consist of many materials, limited primarily by the capacity to link organic molecules and the compatibility of the solid support with the conditions encountered during the synthetic steps. Suitable support materials typically will include, but are not limited to, the types of material typically utilized in peptide and polymer synthesis and include porous glass, $SiO_2$, $Al_2O_3$, clays, graphite, cross-linked polystyrene or similar polymers including macro and microporous polymers and gels, dendrimers, linear organic polymers, e.g. polyethyleneglycol, polystyrene- or polymethacrylate-dimethylacrylamide copolymer pins, and other materials known to those skilled in the art. The chemically reactive groups with which the solid supports may be derivatized are those commonly used for the solid phase synthesis of polymers and peptides and thus well known to those skilled in the art. To improve washing efficiencies, one can employ nonporous supports less porous than typical peptide synthesis supports. For certain applications, however, quite porous beads, resins, or other supports work well and may be preferable. Particularly preferred resins include Merrifield resin, hydroxymethyl polystyrene resins; Wang resin; ArgoGel (available from Argonaut, S. San Francisco, Calif.); Sasrin resin (Bachem Bioscience, Switzerland); and TANTAGEL S AC, TANTAGEL PHB, or TANTAGEL S NH2 resin (polystyrene-polyethyleneglycol copolymer resins available from Rappe Polymere, Tubingen, Germany). Other preferred supports are commercially available and described by Novabiochem, La Jolla, Calif.

One object of the present invention is a process for preparing a plurality (library) of polypyrrolinone derivatives of formula (38):

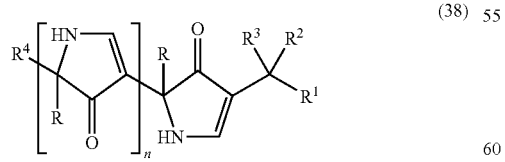
(38)

wherein:
R is independently selected from a group consisting of a straight $C_1$-$C_6$ alkyl, a branched $C_3$-$C_7$ alkyl, $C_3$-$C_7$ cycloalkyl, a straight $C_1$-$C_6$ alkenyl, a branched $C_3$-$C_7$ alkenyl, $C_1$-$C_4$ hydroxyalkyl, $C_1$-$C_4$ thioalkyl, $C_1$-$C_4$ methylthioalkyl, —$(CH_2)_oN(R^5)_2$, —$(CH_2)_oCO_2H$, —$(CH_2)_oCON(R^5)_2$, phenyl optionally substituted with one to three hydroxyl, lower alkoxy, halo, nitro, or cyano groups, $C_7$-$C_{12}$ benzyl optionally substituted with the same groups as above or heteroaryl;

$R^1$ is hydrogen, hydroxyl, lower alkoxy, amino or alkoxycarbonyl-protected amino;

$R^2$ is R, carboxyl, a carbonyl linked to a solid support or alkoxycarbonyl;

$R^3$ is R or hydrogen;

$R^4$ is R or (46);

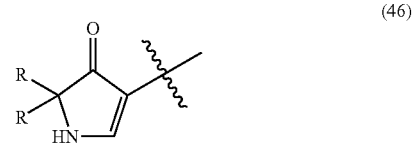
(46)

$R^5$ is hydrogen or lower alkyl;

n is 0 to 3;

o is 1 to 4.

The R substituent on the pyrrolinone ring corresponds to the side chain of an individual amino acid in a polypeptide and the present invention should be seen to extend to a method to prepare peptidomimetics of both natural and unnatural amino acids along with salts of acidic or basic atoms, hydrates, solvates and clathrates.

One specific embodiment on the present invention is an improved process for preparing a polypyrrolinones comprising the following steps:

(a) exposing an α-amino-α-substituted-1,4-dioxo compound (39), optionally with an alkoxycarbonyl protecting group, to a plurality of treatments with a 2-substituted-2-aminovalerolactone, trimethylorthoformate, optionally in the presence of a solvent, to produce imine (40)

wherein:
$R^6$ is an amino protecting group, $R^7$ is a $C_1$-$C_4$ alkoxy or a carboxyl or carbamido linked to a solid support, or $R^6$ and $R^7$ together form a pyrrolinone ring;

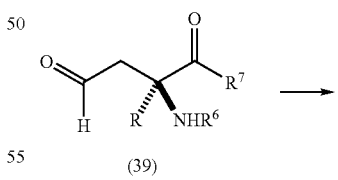
(39)

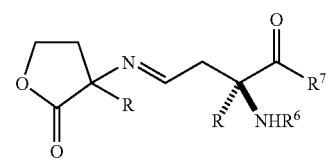
(40)

(b) cyclizing (40) by forming metalloimine carbanion with base optionally in the presence of a crown ether to form a pyrrolinone (41);

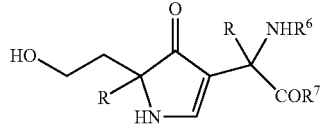

(41)

(c) oxidizing the primary alcohol to the corresponding aldehyde;

(d) repeating steps (a)-(c) m times to produce polypyrrolinone (42);

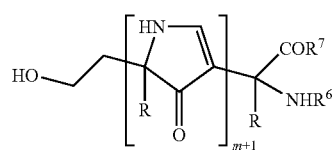

(42)

(e) terminating the synthesis by repeating steps (a) through (c) using α-substituted amino acid in place of the valerolactone in step (b) to yield (43).

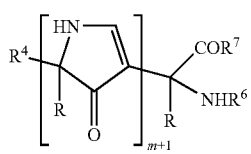

Figure 2:
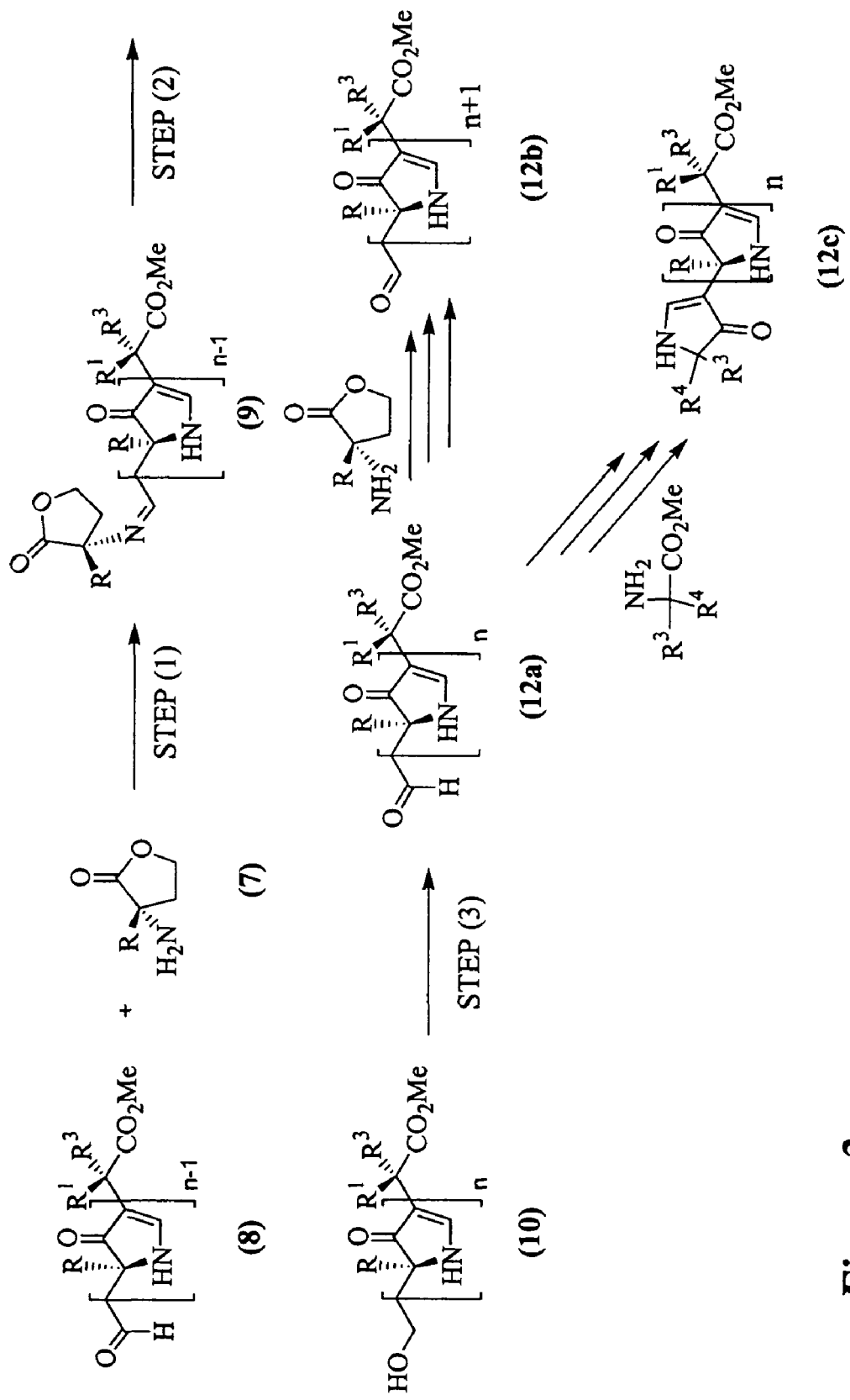
FIG. 2 shows a new solution phase synthesis using α-aminovalerolactone synthons for introduction of the carbon skeleta.

(43)

α-Aminovalerolactone derivatives have now been found to be useful synthons for incorporating the required elements for a pyrrolinone ring while simultaneously introducing a latent aldehyde required for each iterative cycle (FIG. 2). In step (1) the intermediate imine is formed by azeotropic removal of water from a solution of containing an aminovalerolactone (7) derivative and an aldehyde derivative or, preferably, by stirring the aminovalerolactone and aldehyde with trimethylorthoformate to remove the water, optionally in the presence of a solvent. The aminovalerolactone derivative will generally optionally possess an additional α-substituent which corresponds to the side chain of an amino acid.

Figure 3:
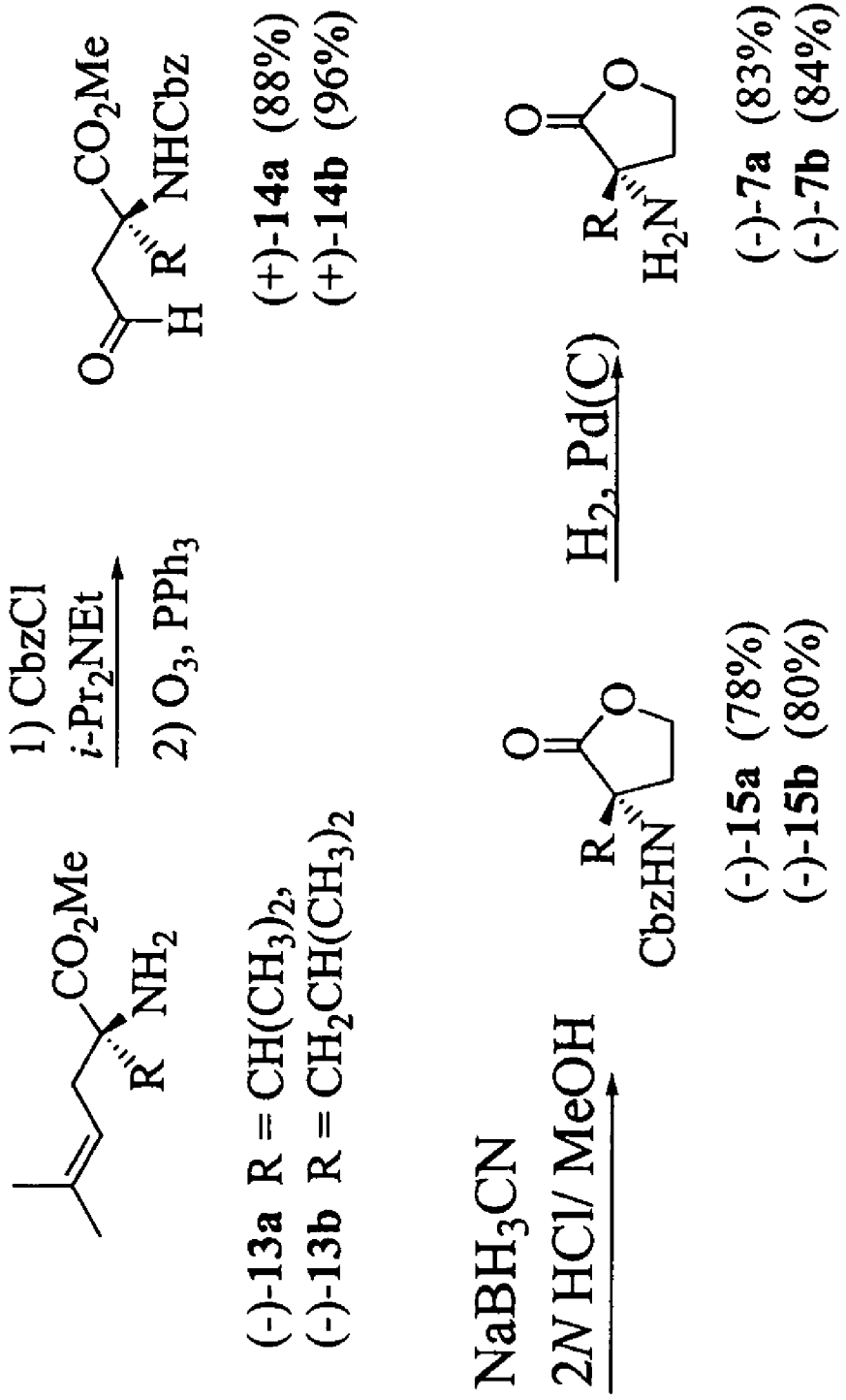
FIG. 3 shows a method for the preparation of chiral α-aminovalerolactone synthons.

The requisite valerolactones are prepared (FIG. 3) in four steps from optionally chiral 5-methyl-hex-4-enoic acid derivatives which are described in U.S. Pat. No. 6,034,247 which is incorporated herein by reference in its entirety. The amino group is protected with benzyl chloroformate and the olefin side chain oxidized with ozone to furnish amino aldehydes (+)-14 in >88% yield (two steps). Reduction with sodium cyanoborohydride (2 N HCl/methanol) proceeded with concomitant cyclization to furnish Cbz-protected aminolactones (−)-15. Hydrogenolysis of the benzyl group removes the protecting group and produces the desired aminolactone (−)-7.

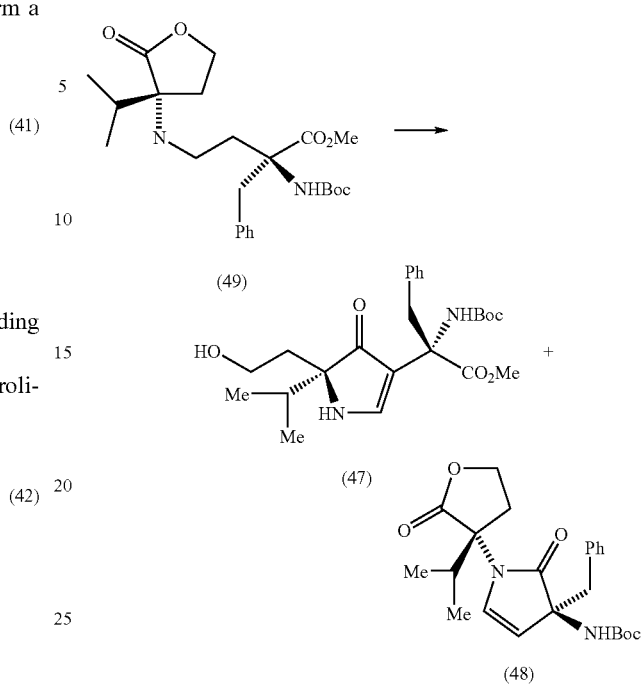

To successfully adapt the synthesis from solution phase to solid phase conditions were required to carry out the desired cyclization efficiently on a solid support. When the model compound (46) was treated with lithium alkylamides, e.g. LDA, LTMP and LiHMDS, the undesired unsaturated lactam (48) is a major side product (ca. 40%) which presumably arises by addition of the metalloimine nitrogen to the carbomethoxy group. Reacting (46) with excess KHMDS (8 equiv) in the presence of 18-crown-6 (8 equiv) produced a red solution which was stirred for 2 hours at 0° C., 3 hours at room temperature, and then quenched with 5% aq. NaHSO4 to furnish hydroxypyrrolinone (−)-47 in 77% yield (2 steps). In the absence of 18-crown-6, the yield of (−)-47 was 55%. When KHMDS/18-crown-6 was employed, lactam (−)-48 was formed in less then 5% yield. This reaction has now been found to be generally applicable to polypyrrolinones (FIG. 2; step 2).

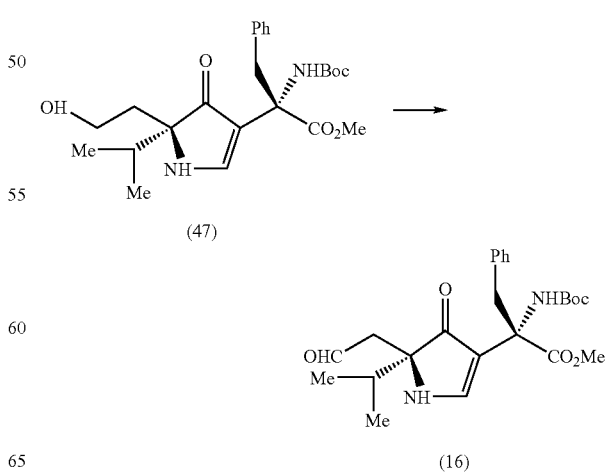

| Conditions | (−)-16, % yield |
|---|---|
| Dess Martin | 26 |
| Dess Martin, pyridine | 39 |
| SO$_3$/pyr, DMSO, Et$_3$N(4:1) | 25 |
| SO$_3$/pyr, DMSO, i-Pr$_2$NEt | decomposition |
| (COCl)$_2$, DMSO, Et$_3$N | 46 |
| (COCl)$_2$, DMSO, i-Pr$_2$NE | 87 |
| (COCl)$_2$, DMSO, DBU | 85 |

Ring-opening of the valerolactone (FIG. 2) in step (2) concomitantly produces a primary alcohol which can be conveniently employed to regenerate the aldehyde and initiate the next iterative cycle thereby circumventing the problematical OsO$_4$-catalyzed process. Many common and efficient oxidizing agents and conditions, including the Dess-Martin periodinane (Dess, D. B. and Martin, J. C., *J. Org. Chem.*, (1983) 48:2115; Ireland, R. E. and Liu, L., *J. Org. Chem.*, (1993) 58:1129) and the Parikh-Doering sulfur trioxide-pyridine complex failed to produce the desire alcohol in good yield. Surprisingly the Swern oxidation employing DBU or Hunig's base generated the desired aldehyde (16) in 85% yield. DBU proved to be the best choice for polypyrrolinone sythesis (FIG. 3; step 3) since Hunig's base produced a minor byproduct. These conditions were easily adapted to the iterative synthesis of polypyrrolinones (FIG. 2; 12a-12c)

Figure 4:
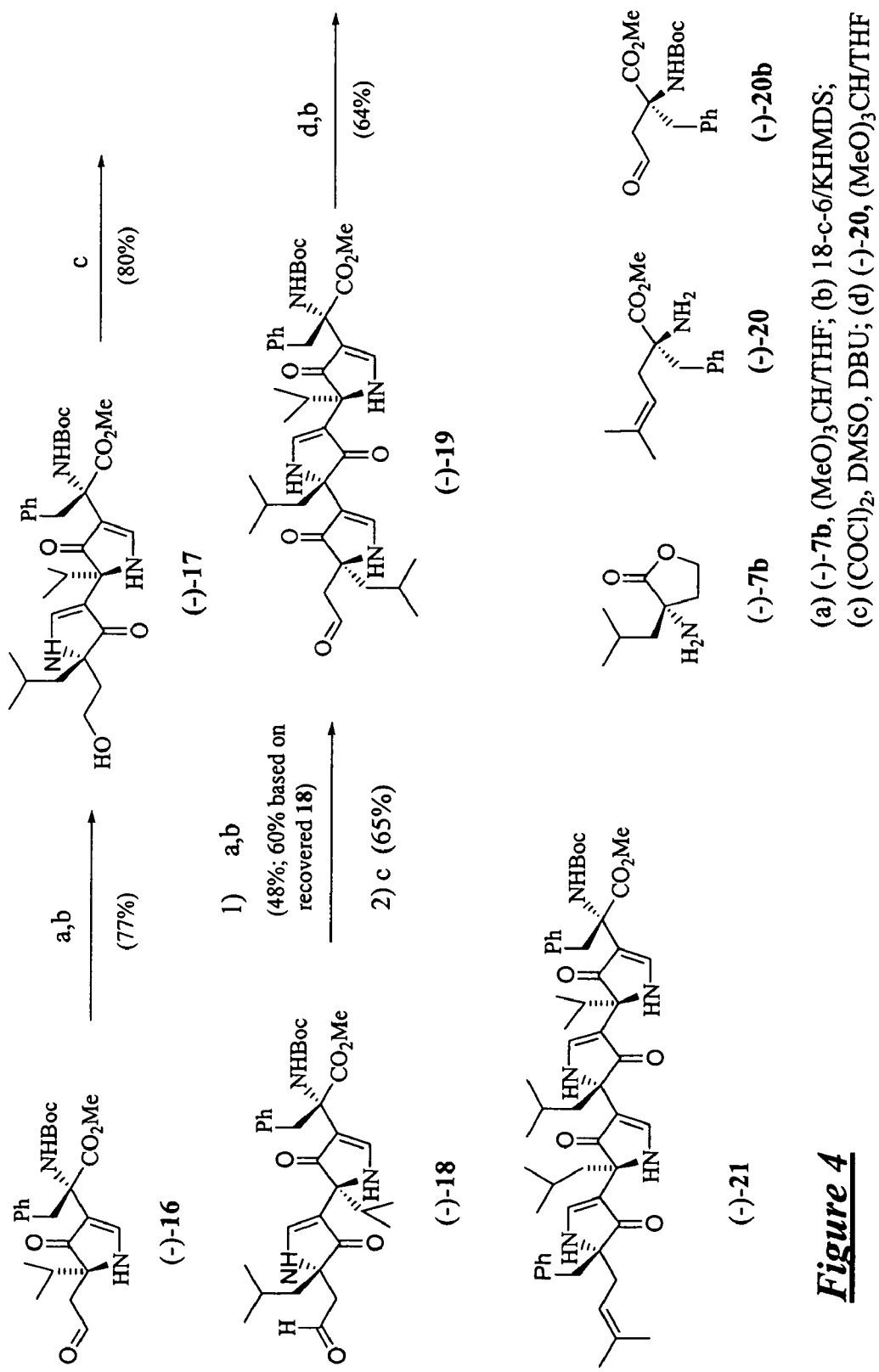
FIG. 4 shows a synthesis of tetra-pyrrolinones using α-aminovalerolactone synthons.

The generality and applicability of these conditions for the preparation of extended polypyrrolinnone was established by the preparation of the tetra-pyrrolinone (21) as depicted in FIG. 4. Two iterations of the aforementioned 3-step protocol (e.g., imine formation, metalloimine cyclization and Swern oxidation) furnished tris-pyrrolinone aldehyde (−)-19 in 19% overall yield for the 6 steps. Significantly improved yields were obtained when imine formation was carried out at room temperature for 12 h with a 1:1 (v/v) mixture of trimethyl orthoformate (Look, G. C. et al., Tetrahedron Lett, (1995) 36:2935; Ruhland, B. *J. Am. Chem. Soc.* 1995, 118: 9947) and THF. Tris-pyrrolinone aldehyde (−)-19 was then capped with aminoester (−)-20 derived from phenylalanine to furnish tetra-pyrrolinone (−)-21 (64% yield), identical in all aspects with an authentic sample prepared by solution phase synthesis. (Smith, A. B., III et al., *J. Am. Chem. Soc.* 1994, 116:9947)

In a second embodiment of the present invention there is provided a solid-phase process for the synthesis of polypyrrolinones wherein R$^7$ is a carboxyl or carbamido group linked to a solid support during the process which further comprises the following additional steps:

(f) attaching a latent aldehyde (40) to a solid support and converting the latent aldehyde to an aldehyde (41);

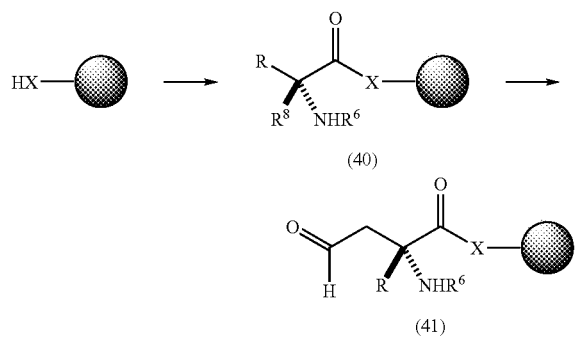

wherein:
R$^8$ is 3-methyl-1-but-2-enyl, 2,2-dimethoxyethyl, 2-hydroxyethyl, and
X is nitrogen or oxygen;
(g) repeating steps (a)-(c) m times and terminating the synthesis as in step (e) (supra) to produce polypyrrolinone (42);

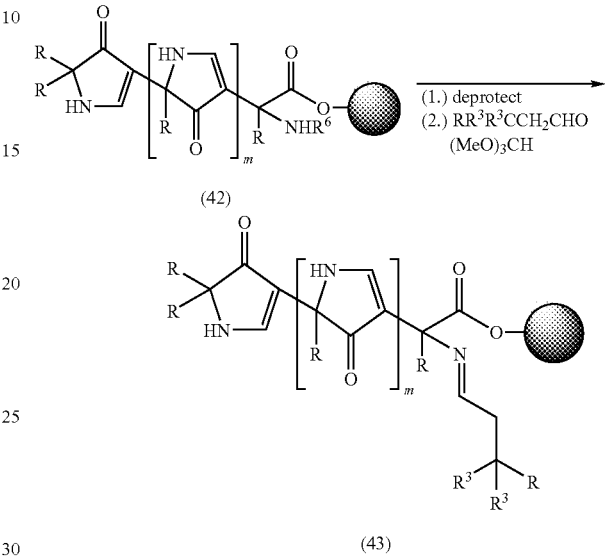

(h) cleaving the polypyrrolinone from the resin by deprotecting the α-amino group, and exposing the α-amino acid to a plurality of treatments with an aldehyde, trimethylorthoformate, optionally in the presence of a solvent, to produce the corresponding imine (43); and, (i) cyclizing (43) by forming the metalloimine carbanion with base, optionally in the presence of a crown ether, to produce a pyrrolinone (44);

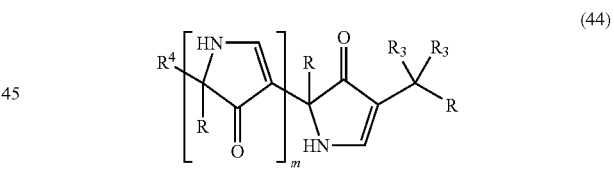

In order to adapt the solution phase polypyrrolinone synthesis to solid phase, two additional synthetic operations must be incorporated into the process. Firstly, at the outset of the process the first reactant must be linked to a solid support. One preferred embodiment of the current invention uses divinylbenzene cross-linked resin beads. In a particular embodiment the first reactant is attached to Wang resin. The Wang resin is comprised of p-hydroxybenzyl alcohol linkers. Methodology to link carboxylic acids to cross-linked DVB resins has been extensively refined for peptide synthesis and optimized conditions are well known to the skilled artisan. (Atherton, E. and Sheppard, R. C., *Solid Phase Peptide Synthesis,* 1989, IRL Press, Oxford)

Secondly, a process is required to release the final product from the solid support (step h and step i). A variety of strategies for releasing the final product in the final step of the synthesis have been developed (Obrecht D. and Villalgordo J. M., *Solid Supported Combinatorial and Parallel Synthesis of*

Small-Molecular-Weight Compound Libraries, 1998, Tetrahedron Organic Chemistry Series, vol. 17, Pergamon Press, Oxford). Particularly useful and applicable to the present process is cyclization-assisted cleavage wherein addition of a new pyrrolinone ring and resin cleavage occur in a single step. This process ideally is specific and results in only cleavage of α-amino esters. The product in solution after filtration of the solid support should require minimal purification. In the present process the α-amino ester affords the opportunity to utilize the metalloenamine cyclization to elaborate a pyrrolinone ring and simultaneously cleave the polypyrrolinone chain from the resin.

The Teoc-protected amino acid (+)-22 (1.1 equiv) was attached to Wang resin via the Mitsunobu reaction to provide resin bound amino ester 23. (FIG. 5) Removal of the Teoc-protecting group (TBAF) afforded amino ester 24 bound to the resin, which was condensed with hydrocinnamaldehyde ($PhCH_2CH_2CHO$) in the presence of trimethyl orthoformate and THF to drive imine formation to completion 25. Reacting imine 25 with KHMDS (10 equiv) led via metalloenamine, to cyclization of the pyrrolinone ring and simultaneous traceless release from the resin. Flash chromatography furnished known monopyrrolinone (−)-21 in 62% yield (4 steps; average yield/step 89%).

Figure 5:
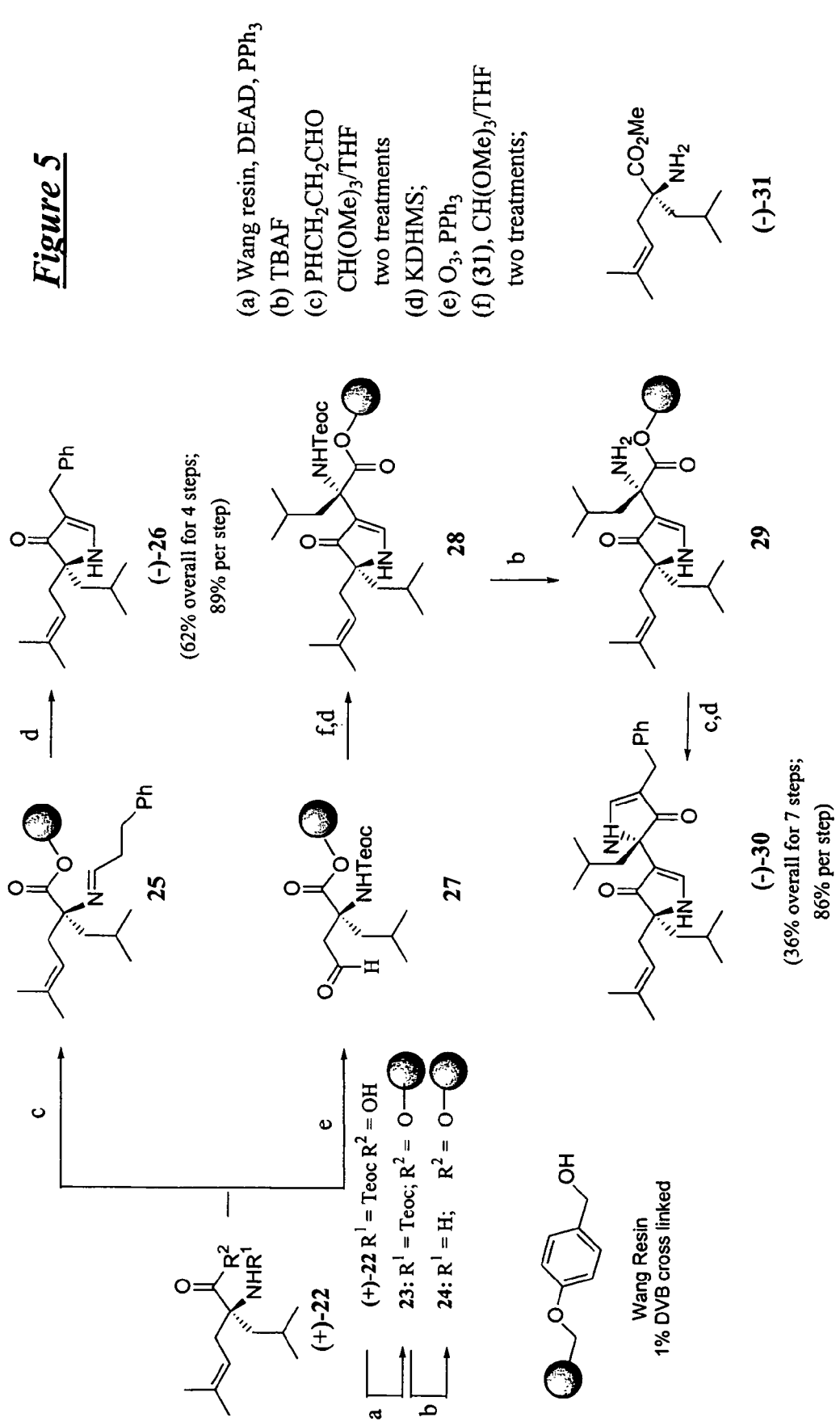
FIG. 5 shows a solid phase synthesis of pyrrolinones.

To prepare the starting material for extended polypyrrolinones the Teoc-protected amino acid was oxidatively cleaved with ozone to yield the 1,4-dicabonyl derivative 27 (FIG. 5). Imine formation with amino ester (−)-31 followed by KHMDS promoted metalloimine cyclization produced the mono-pyrrolinone (28). Fluoride-mediated cleavage of the Teoc group (TBAF), followed in turn by imine formation with hydrocinnamaldehyde and metalloimine formation with KHMDS again led to cyclization and resin release to furnish known bis-pyrrolinone (−)-30 in 36% isolated yield for the 7 steps (average yield/step 86%).

Figure 6:
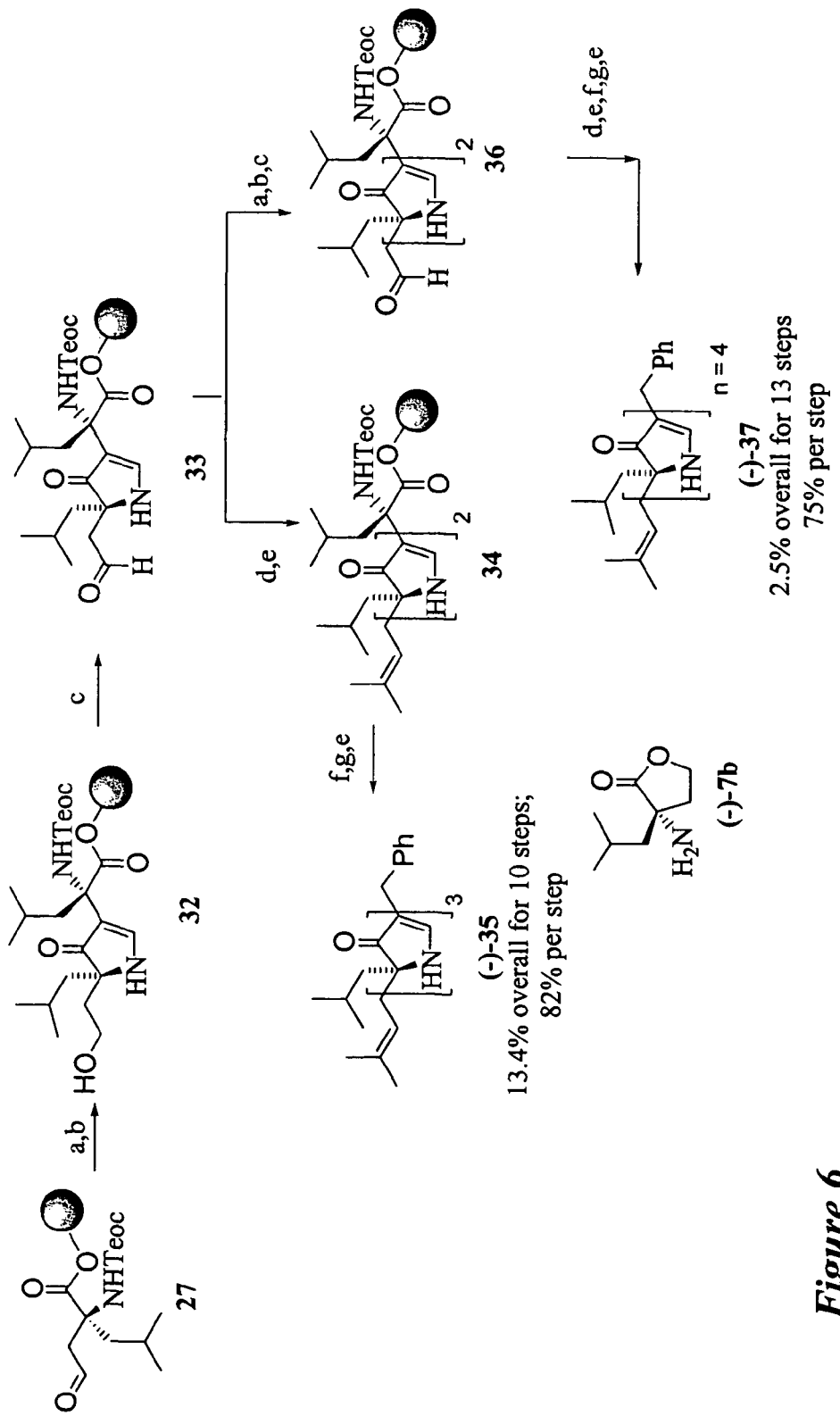
FIG. 6 shows a solid phase synthesis of tris-pyrrolinones and tetra-pyrrolinones.

To further establish the generality of the protocol the synthesis was extended to tris- and tetra-pyrrolinones. (FIG. 6) The resin-bound aldehyde was first treated with the aminovalerolactone 7b to elaborate the first pyrrolinone. The second ring was constructed using the end-capping procedure with an α-substituted amino ester 31 and the final ring was put in place by intramolecular hydrocinnamaldehyde mediated cyclization/resin cleavage process. The tris-pyrrolinone (−)-35 was isolated in 13.4% yield (10 steps; average yield/step 82%). Significantly, this yield was higher than both those obtained from the dimethyl acetal (8.4%) and the $OsO_4$/$NaIO_4$ oxidation (9.1%) protocols.

Finally, the aminolactone approach to polypyrrolinones was extended to tetra-pyrrolinone (−)-37. Thus, beginning with resin bound aldehyde 27, two iterations of the α-aminovalerolactone procedure wit (−)-7b produced (36). Subsequent end-capping with (−)-31 introduced the third pyrrolinone ring and cyclization-assisted cleavage with hydrocinnamaldehyde elaborated the final ring. tetra-pyrrolinone (−)-37 was obtained in 2.5% overall yield (13 steps) after flash chromatography along with a 2.9% yield of tris-pyrrolinone (−)-35 which appears to arise from the incomplete conversion of 33 to 36.

General Experimental Procedures

All solution phase reactions were carried out in oven-dried or flame-dried glassware under an argon atmosphere, unless otherwise noted. All solvents were reagent or high performance liquid chromatography (HPLC) grade. Diethyl ether and tetrahydrofuran (THF) were freshly distilled from sodium/benzophenone under argon prior to use. Dichloromethane was freshly distilled from calcium hydride before use. Triethylamine and diisopropylethylamine were distilled from calcium hydride and stored over potassium hydroxide. HPLC grade benzene was purchased from J. T. Baker and stored over 4 Å molecular sieves. Anhydrous dimethylformamide and dimethyl sulfoxide were purchased from Aldrich and used without purification. Commercial n-Butyllithium solutions were standardized by titration with diphenylacetic acid. Wang resin (100-200 mesh, 1% DVB cross linked) was purchased from Novabiochem, the loading level is 0.83 mmol/g. All solid phase reactions were vortexed using a Mistral multi-mixer.

Unless otherwise stated, all reactions were magnetically stirred and monitored by thin layer chromatography using 0.25 mm E. Merck pre-coated silica gel plates. Flash column chromatography was performed with the indicated solvents using silica gel-60 (particle size 0.040-0.062 mm) supplied by E. Merck. Yields refer to chromatographically and spectroscopically pure compounds, unless otherwise stated.

All melting points were determined on a Bristoline heated-stage microscope or a Thomas-Hoover apparatus and are corrected. The IR and NMR spectra were obtained for $CHCl_3$ and $CDCl_3$ solutions respectively unless otherwise noted. Infrared spectra were recorded with a Perkin-Elmer Model 283B spectrometer using polystyrene as an external standard. Proton and $^{13}C$ NMR spectra were recorded on a Bruker AM-500 spectrometer and obtained at 305 K unless otherwise noted. Chemical shifts are reported relative to chloroform ($\delta$ 7.24 for proton and $\delta$ 77.0 for $^{13}C$). Optical rotations were obtained with a Perkin-Elmer model 241 polarimeter in the solvent indicated. High-resolution mass spectra were obtained at the University of Pennsylvania Mass Spectrometry Service Center on either a VG micromass 70/70H high resolution double-focusing electron impact/chemical ionization spectrometer or a VG ZAB-E spectrometer.

EXAMPLE 1

Preparation of Cbz-protected Amino Aldehyde (+)-14a

To a 0° C. solution of (−)-13a (2.30 g, 11.55 mmol) in THF (40 mL) was added i-$Pr_2NEt$ (2.41 mL, 1.79 g, 13.86 mmol) followed by benzyl chloroformate (1.81 mL, 2.17 g, 12.7 mmol). The mixture was warmed to rt, stirred for 4 h, cooled back to 0° C., and quenched by addition of 2 N aqueous HCl (20 mL). The resulting biphasic mixture was warmed to rt, extracted with EtOAc (2×50 mL), and the combined organic phases washed with 2 N aqueous HCl (10 mL), saturated aqueous $NaHCO_3$ (15 mL), brine (15 mL), dried over anhydrous $MgSO_4$, and concentrated in vacuo. The resulting oil was purified by flash chromatography (EtOAc/hexanes, 5:95) to afford the Cbz-protected amino ester (3.56 g, 93% yield) as a colorless oil: $[\alpha]_D^{23}$+16.8° (c 1.0, $CHCl_3$); IR (KBr) 3600, 3500, 1720, 1500 $cm^{-1}$; $^1H$ NMR (500 MHz, $CDCl_3$) δ 7.40-7.25 (m, 5H), 5.78 (bs, 1H), 5.88 (d, 1H, J=12.4 Hz), 5.01 (d, 1H, J=12.4 Hz), 4.86 (t, 1H, J=6.7 Hz), 3.71 (s, 3H), 3.12 (dd, 1H, J=6.2, 7.2 Hz), 2.64 (dd, 1H, J=6.2, 7.2 Hz), 2.48 (heptet, 1H, J=6.4 Hz), 1.62 (s, 3H), 1.53 (s, 3H), 0.97 (d, 3H, J=6.9 Hz), 0.89 (d, 3H, J=6.9 Hz); $^{13}C$ NMR (125 MHz, $CDCl_3$) δ 173.38, 154.21, 136.87, 135.08, 128.44, 127.93, 127.86, 118.36, 67.47, 66.10, 52.20, 33.80, 31.02, 25.96, 17.82, 17.77; high-resolution mass spectrum (CI, $NH_3$) m/z 334.2026 [$(M+H)^+$], calcd for $C_{19}H_{28}NO_4$ 334.2018.

A solution of Cbz-protected amino ester (6.8 g, 20.4 mmol) in $CH_2Cl_2$ (70 mL) was cooled to −78° C., and ozone was bubbled into the reaction until a blue color persisted. After excess ozone was purged with argon, PPh$_3$ (5.88 g, 22.43 mmol) was added, and the solution was warmed to rt, stirred for 14 h, and concentrated in vacuo. The resulting oil was purified by flash chromatography (EtOAc/hexanes, 20:80) to afford (+)-14a (5.95 g, 95% yield) as a colorless oil: $[\alpha]_D^{23}$+ 0.19° (c 1.1, CHCl$_3$); IR (KBr) 3620, 3400, 1730, 1225 cm$^{-1}$; $^1$H NMR (500 MHz, CDCl$_3$) δ 9.66 (s, 1H), 7.33-7.29 (m, 5H), 5.89 (bs, 1H), 5.05-4.98 (m, 2H), 3.79 (bs, 1H), 3.74 (s, 3H), 3.07 (d, 1H, J=17.7 Hz), 2.35 (heptet, 1H, J=7.0 Hz), 0.91 (d, 3H, J=6.6 Hz), 0.90 (d, 3H, J=6.6 Hz); $^{13}$C NMR (125 MHz, CDCl$_3$) δ 199.2, 172.0, 154.7, 136.3, 128.5, 128.1, 127.8, 66.5, 63.2, 52.7, 46.2, 34.6, 17.5, 17.2; high-resolution mass spectrum (CI, NH$_3$) m/z 308.1493 [(M+H)$^+$], calcd for C$_{16}$H$_{22}$NO$_5$ 308.1498.

EXAMPLE 2

Preparation of Cbz-protected Amino Aldehyde (+)-14b

Following the procedure described above for (+)-14a; flash chromatography (EtOAc/hexanes, 20:80) afforded (+)-14b (5.90 g, 96% yield for two steps); compound (+)-14b has physical and spectroscopic properties identical to literature values (Smith, A. B. III, et al., *J. Am. Chem. Soc.* (1994) 116: 9947).

EXAMPLE 3

Preparation of Cbz-protected Amino Lactone (−)-15a

Typical Procedure for Reduction With NaCNBH$_3$

To a 0° C. solution of (+)-14a (2.15 g, 7.0 mmol) in MeOH (10 mL) was added NaBH$_3$CN (0.65 g, 10.5 mmol) in small portions over a period of 10 min. To this mixture 2N HCl in MeOH (55 mL) was added and the mixture was warmed to rt, stirred for 3 h, diluted with EtOAc (400 mL), and basified to pH 9 with saturated aqueous NaHCO$_3$. The resulting biphasic mixture was extracted with EtOAc (2×200 mL), and the combined organic phases washed with brine (100 mL), dried over anhydrous MgSO$_4$, and concentrated in vacuo. The resulting oil was purified by flash chromatography (EtOAc/hexanes, 40:60) to afford (−)-15a (1.6 g, 78% yield) as a white crystalline solid: mp 73-75° C.; $[\alpha]_D^{23}$−3.6° (c 0.67, CHCl$_3$); IR (KBr) 3447, 1772, 1719 cm$^1$; $^1$H NMR (500 MHz, CDCl$_3$) δ 7.40-7.29 (m, 5H), 5.17 (bs, 1H), 5.12-5.04 (m, 2H), 4.52 (bs, 1H), 4.23-4.14 (m, 1H), 2.64-2.54 (m, 1H), 2.45-2.38 (m, 1H), 2.14-2.07 (m, 1H), 1.02 (d, 3H, J=6.9 Hz), 0.99 (d, 3H, J=6.8 Hz); $^{13}$C NMR (125 MHz, CDCl$_3$) δ 177.0, 155.2, 135.8, 128.5, 128.3, 128.2, 67.1, 65.6, 62.6, 33.9, 29.1, 17.1, 16.4; high-resolution mass spectrum (CI, NH$_3$) m/z 278.1394 [(M+H)$^+$], calcd for C$_{15}$H$_{20}$NO$_4$ 278.1392. Anal. Calcd for C$_{15}$H$_{19}$NO$_4$: C, 64.97; H, 6.91; N, 5.05. Found: C, 65.43; H, 6.69; N, 4.90.

EXAMPLE 4

Cbz-protected Amino Lactone (−)-15b

Following the procedure described above for (−)-15a; flash chromatography (EtOAc/hexanes, 40:60) afforded (−)-15b (1.45 g, 80% yield) as a white solid: mp 62-63° C.; $[\alpha]_D^{23}$− 3.1° (c 0.45, CHCl$_3$); IR (KBr) 3418, 1777, 1719 cm$^{-1}$; $^1$H NMR (500 MHz, CDCl$_3$) δ 7.41-7.29 (m, 5H), 5.30 (bs, 1H), 5.12-5.06 (m, 2H), 4.46 (bs, 1H), 4.25 (dd, 1H, J=8.8, 16.6 Hz), 2.72-2.68 (m, 1H), 2.54-2.50 (m, 1H), 1.86-1.79 (m, 2H), 1.70-1.63 (m, 1H), 0.97 (d, 3H, J=6.3 Hz), 0.94 (d, 3H, J=6.3 Hz); $^{13}$C NMR (125 MHz, CDCl$_3$) δ 176.9, 154.8, 136.0, 128.5, 128.2, 128.1, 66.9, 65.5, 58.8, 43.6, 34.3, 24.3, 24.0, 23.6; high-resolution mass spectrum (CI, NH$_3$) m/z 292.1560 [(M+H)$^+$], calcd for C$_{16}$H$_{22}$NO$_4$ 292.1549. Anal. Calcd for C$_{16}$H$_{21}$NO$_4$: C, 65.97; H, 7.27; N, 4.81. Found: C, 65.94; H, 7.30; N, 4.78.

EXAMPLE 5

Preparation of Amino Lactone (−)-7a

Typical Procedure for Removal of the Cbz Protecting Group

A heterogeneous mixture of (−)-15a (3.43 g, 12.4 mmol) and Pd(C) (0.05 g) in EtOH (110 mL) was treated with H$_2$ (balloon) for 1 h. The crude mixture was filtered through a short silica column to remove the catalyst and the filtrate was concentrated in vacuo. Purification by flash chromatography (EtOAc) afforded (−)-7a (1.48 g, 83% yield) as a colorless oil: $[\alpha]_D^{23}$−46.3° (c 0.54, CHCl$_3$); IR (neat) 3350, 2960, 1770, 1220 cm$^{-1}$; $^1$H NMR (500 MHz, CDCl$_3$) δ 4.344.30 (m, 1 H), 4.24-4.20 (m, 1H), 2.37-2.31 (m, 1H), 1.97-1.91 (m, 2H), 1.03 (d, 3H, J=6.8 Hz), 0.95 (d, 3H, J=6.8 Hz); $^{13}$C NMR (125 MHz, CDCl$_3$) δ 180.6, 64.9, 61.0, 34.0, 31.8, 17.6, 16.2; high-resolution mass spectrum (CI, NH$_3$) m/z 144.1020 [(M+H)$^+$], calcd for C$_7$H$_{14}$NO$_2$ 144.1025. Anal. Calcd for C$_7$H$_{13}$NO$_2$: C, 58.72; H, 9.15. Found: C, 58.31, H, 9.02.

EXAMPLE 6

Amino Lactone (−)-7b

Following the procedure described Example 5; flash chromatography (EtOAc) afforded (−)-7b (0.58 g, 84% yield) as a colorless oil: $[\alpha]_D^{23}$−36.3° (c 3.1, CHCl$_3$); IR (neat) 3460, 1770, 1220 cm$^{-1}$; $^1$H NMR (500 MHz, CDCl$_3$) δ 4.30-4.24 (m, 1H), 4.194.13 (m, 1H), 2.29-2.24 (m, 1H), 2.08-2.03 (m, 1H), 1.84-1.77 (m, 1H), 1.60 (dd, 1H, J=5.3, 14.3 Hz), 1.43 (dd, 1H, J=7.1, 14.4 Hz), 0.93 (d, 3H, J=6.6 Hz), 0.90 (d, 3H, J=6.7 Hz); $^{13}$C NMR (125 MHz, CDCl$_3$) δ 180.9, 64.6, 57.4, 45.7, 35.6, 24.6, 24.1, 23.6; high-resolution mass spectrum (CI, NH$_3$) m/z 158.1178 [(M+H)$^+$], calcd for C$_8$H$_{16}$NO$_2$ 158.1181. Anal. Calcd for C$_8$H$_{15}$NO$_2$: C, 61.12; H, 9.62. Found: C, 60.89, H, 9.54.

EXAMPLE 7

Preparation of Monohydroxy Pyrrolinone (−)-47

Solutions of aminolactone (−)-7a (68 mg, 0.47 mmol) and aldehyde (−)-20b (FIG. 4) (138 mg, 0.43 mmol) in toluene (5 mL each) were combined and concentrated in vacuo, and the residue azeotropically dehydrated with additional toluene (3×10 mL). The resultant oil was dissolved in THF (15 mL), and this solution was added via cannula to a solution of KHMDS (6.9 mL, 3.44 mmol, 0.5 M in toluene) and 18-c-6 (909 mg, 3.44 mmol) in THF (35 mL) at 0° C. The resultant reddish solution was stirred at 0° C. for 2 h, at rt for 3 h, cooled back to 0° C., and quenched by addition of 5% aqueous NaHSO$_4$ (10 mL). The mixture was then warmed to rt, stirred for another 20 min, and then extracted with EtOAc (3×25 mL). The combined organic extracts were washed with saturated aqueous NaHCO$_3$ and brine (15 mL each), dried over anhydrous MgSO$_4$, and concentrated in vacuo. Flash chromatography (EtOH/EtOAc/hexanes 10:40:50) afforded (−)-

47 (148 mg, 77% yield) as a white solid: mp 190° C. dec; $[\alpha]_D^{23}$ −10.2° (c 0.48, CHCl$_3$); IR (CHCl$_3$) 3447, 1751, 1685, 1636 cm$^{-1}$; $^1$H NMR (500 MHz, CDCl$_3$) δ 8.26 (d, 1H, J=3.8 Hz), 7.23-7.19 (m, 3H), 7.04-7.00 (m, 2H), 6.27 (bs, 1H), 5.87 (bs, 1H), 3.79 (d, 1H, J=13.2 Hz), 3.70 (s, 3H), 3.49-3.42 (m, 2H), 3.29 (d, 1H, J=13.1 Hz), 2.50 (bs, 1H), 2.07-1.94 (m, 2H), 1.81-1.76 (m, 1H), 1.42 (s, 9H), 0.95 (d, 3H, J=6.9 Hz), 0.74 (d, 3H, J=6.7 Hz); $^{13}$C NMR (125 MHz, CDCl$_3$) δ 202.1, 172.0, 163.7, 154.7, 135.6, 130.0, 128.1, 127.0, 112.8, 79.4, 73.2, 60.0, 58.7, 52.6, 39.3, 37.2, 34.1, 28.4, 16.9, 15.9; high-resolution; mass spectrum (ES, Na$^+$) m/z 447.2476 [(M+H)$^+$], calcd for C$_{24}$H$_{35}$N$_2$O$_6$ 447.2495. Anal. Calcd for C$_{24}$H$_{34}$N$_2$O$_6$: C, 64.55; H, 7.67. Found: C, 64.25; H, 7.33. Also isolated was unsaturated lactam (−)-48: mp 169-170° C.; $[\alpha]_D$-8.4° (c 0.87, CHCl$_3$); IR (KBr) 3374, 1718, 1702, 1171 cm$^{-1}$; $^1$H NMR (500 MHz, CDCl$_3$) δ 7.28-7.21 (m, 3H), 7.15-7.12 (m, 2H), 6.66 (d, 1H, J=5.2 Hz), 5.60 (d, 1H, J=5.2 Hz), 4.93 (bs, 1H), 4.18-4.10 (m, 1H), 4.03-3.98 (m, 1H), 3.12-3.04 (m, 1H), 3.06 (d, 1H, J=12.9 Hz), 2.89 (d, 1H, J=12.8 Hz), 2.38-2.31 (m, 1H), 2.27-2.22 (m, 1H), 1.40 (s, 9H), 1.00 (d, 3H, J=6.8 Hz), 0.88 (d, 3H, J=6.8 Hz); $^{13}$C NMR (125 MHz, CDCl$_3$) δ 178.4, 173.5, 154.1, 133.8, 130.8, 130.3, 128.1, 127.3, 111.1, 80.2, 65.8, 65.7, 64.4, 42.9, 33.2, 29.0, 28.3, 17.1, 16.7; high-resolution mass spectrum (CI, NH$_3$) m/z 414.2148 [M$^+$], calcd for C$_{23}$H$_{30}$N$_2$O$_5$ 414.2155. Anal. Calcd for C$_{23}$H$_{30}$N$_2$O$_5$: C, 66.65; H, 7.30. Found: C, 66.55; H, 7.28.

EXAMPLE 8

Preparation of Monopyrrolinone Aldehyde (−)-16

Typical Procedure for the Swern Oxidation of Hydroxy Pyrrolinones

To a solution of (COCl)$_2$ (0.31 mL, 0.61 mmol, 2.0 M in CH$_2$Cl$_2$) in CH$_2$Cl$_2$ (15 mL) at −70° C. was added DMSO (0.1 mL, 95 mg, 1.22 mmol). The resulting solution was stirred for 15 min, cooled to −78° C., and then a solution of monohydroxy pyrrolinone (−)-47 (182 mg, 0.41 mmol) in CH$_2$Cl$_2$ (10 mL) added via cannula. The reaction was stirred for another 15 min at −78° C. and then DBU (0.30 mL, 310 mg, 2.03 mmol) added via syringe. The solution was warmed to rt, stirred for 20 min, cooled back to 0° C., and quenched by addition of water (5 mL). The resulting biphasic mixture was extracted with CH$_2$Cl$_2$ (2×20 mL). The combined organic extracts were washed with aqueous NaHCO$_3$/brine (1:1, v/v, 2×5 mL), dried over anhydrous MgSO$_4$, and concentrated in vacuo. Flash chromatography (EtOAc/hexanes, 80:20) afforded (−)-16 (154 mg, 85% yield) as a yellow solid; (−)-16 has physical and spectroscopic properties identical to literature values (Smith, A. B. III, et al., *J. Am. Chem. Soc.* (1994) 116: 9947).

EXAMPLE 9

Preparation of Bis-hydroxy Pyrrolinone (−)-17

Typical Procedure for the Synthesis of Hydroxy Pyrrolinones

Solutions of aminolactone (−)-7b (52 mg, 0.33 mmol) and aldehyde (−)-16 (119 mg, 0.27 mmol) in CHCl$_3$ (5 mL each) were combined and concentrated in vacuo, and the residue azeotropically dehydrated with benzene (10 mL). The resultant oil was dissolved in THF (10 mL), followed by addition of trimethylorthoformate (10 mL). The solution was stirred at rt for 14 h and then concentrated in vacuo, and the residue azeotropically dehydrated with toluene (15 mL). The resultant oil was dissolved in THF (13 mL) and this solution added via cannula to a 0° C. solution of KHMDS (4.1 mL, 2.1 mmol, 0.5 M in toluene) and 18-c-6 (650 mg, 2.46 mmol) in THF (20 mL). The reaction was stirred at 0° C. for 2 h, at rt for 4 h, cooled back to 0° C., and quenched by addition of 5% aqueous NaHSO$_4$ (20 mL). The mixture was warmed to rt, stirred for another 20 min and then extracted with EtOAc (3×25 mL). The combined organic extracts were washed with saturated aqueous NaHCO$_3$ and brine (15 mL each), dried over anhydrous MgSO$_4$, and concentrated in vacuo. Flash chromatography (EtOH/EtOAc/hexanes 10:40:50) afforded (−)-17 (120 mg, 77% yield) as a white solid: mp 115-118° C.; $[\alpha]_D^{23}$ −98.7° (c 0.64, CHCl$_3$); IR (KBr) 3460, 3300, 1710, 1640, 1460 cm$^{-1}$; $^1$H NMR (500 MHz, CDCl$_3$) δ 8.23 (bs, 2H), 7.52 (s, 1H), 7.23-7.14 (m, 3 H), 7.04-6.99 (m, 2H), 6.43 (bs, 1 H), 6.25 (bs, 1H), 3.87-3.69 (m, 3H), 3.72 (s, 3H), 3.40 (d, 1H, J=13.2 Hz), 2.32 (bs, 1H), 2.04-1.98 (m, 1H), 1.83 (t, 2H, J=5.6 Hz), 1.74-1.65 (m, 2H), 1.58-1.53 (m, 1H), 1.40 (s, 9H), 0.93 (d, 3H, J=6.9 Hz), 0.83 (d, 3H, J=6.5 Hz), 0.79 (d, 3H, J=6.7 Hz), 0.76 (d, 3H, J=6.3 Hz); $^{13}$C NMR (125 MHz, CDCl$_3$) δ 204.4, 201.0, 172.8, 164.1, 161.3, 154.2, 136.1, 130.1, 128.6, 126.7, 110.6, 107.7, 79.0, 71.4, 70.6, 60.4, 58.7, 52.4, 43.7, 39.8, 39.1, 37.9, 28.4, 24.6, 24.0, 23.8, 17.3, 16.0; high-resolution mass spectrum (ES, Na$^+$) m/z 606.3146 [(M+Na)$^+$], calcd for C$_{32}$H$_{45}$N$_3$O$_7$Na 606.3155. Anal. Calcd for C$_{32}$H$_{45}$N$_3$O$_7$: C, 65.84; H, 7.77. Found: C, 65.53; H, 7.48.

EXAMPLE 10

Bis-pyrrolinone Aldehyde (−)-18

Following the procedure described above for (−)-16 (Example 8), (−)-17 was oxidized to (−)-18; flash chromatography (EtOAc/hexanes, 80:20) afforded (−)-18 (94 mg, 80% yield). Compound (−)-18 has physical and spectroscopic properties identical to literature values (Smith, A. B. III, et al., *J. Am. Chem. Soc.* (1994) 116: 9947).

EXAMPLE 11

Tris-pyrrolinone Aldehyde (−)-19

Following the procedure described above for (−)-17 (Example 9) bis-pyrrolinone aldehyde (−)-18 was converted to tris-pyrrolinone aldehyde (−)-19. The steps on imine formation and metalloenamine cyclization yielded the hydroxyethyl tris-pyrrolinone as a yellow solid (46 mg, 48% yield) after flash chromatography (EtOH/EtOAc/hexanes 10:40:50): mp 130-135° C.; $[\alpha]_D^{23}$ −58.0° (c 0.5, CHCl$_3$); IR (KBr) 3619, 1718, 1654, 1578 cm$^{-1}$; $^1$H NMR (500 MHz, CDCl$_3$) δ 8.21 (bs, 2H), 8.14 (bs, 1H), 7.48 (bs, 1H), 7.42 (bs, 1H), 7.20-7.16 (m, 3H), 7.00-6.97 (m, 2H), 6.55 (bs, 1H), 6.11 (bs, 1H), 3.87-3.80 (m, 1H), 3.78-3.72 (m, 11H), 3.71 (s, 3H), 3.64 (d, 11H, J=12.0 Hz), 3.43 (d, 11H, J=13.1 Hz), 1.96-1.90 (m, 11H), 1.84-1.78 (m, 2H), 1.68-1.48 (m, 6H), 1.40 (s, 9H), 0.85 (d, 3H, J=6.8 Hz), 0.84 (d, 3H, J=6.4 Hz), 0.80 (d, 3H, J=6.4 Hz), 0.78 (d, 3H, J=6.7 Hz), 0.73 (d, 3H, J=6.7 Hz), 0.68 (d, 3H, J=6.6 Hz); $^{13}$C NMR (125 MHz, CDCl$_3$) δ 203.9, 202.6, 201.0, 172.7, 163.9, 161.8, 160.5, 154.3, 136.1, 130.2, 127.9, 126.7, 110.7, 109.4, 107.2, 79.0, 71.2, 70.6, 68.7, 60.7, 58.7, 52.4, 47.4, 43.5, 40.1, 39.3, 37.8, 28.4, 24.7, 24.6, 24.3, 24.1, 23.9, 23.7, 17.1, 15.9; high-resolution mass spectrum (ES, Na$^+$) m/z 721.4162 [(M+H)$^+$], calcd for C$_{40}$H$_{57}$N$_4$O$_8$ 721.4176. Following the procedure described above for (−)-16 (Example 8) the primary alcohol was oxidized to the tris-pyrrolinone aldehyde (−)-19 (28 mg, 65% yield) after flash chromatography (EtOAc/hexanes, 80:20). Compound (−)-19 has physical and spectroscopic properties identical to literature values (Smith, A. B. III, et al., *J. Am. Chem. Soc.* (1994) 116: 9947).

EXAMPLE 12

Tetra-pyrrolinone (−)-21

Following the previously described procedure values (−)-19 was converted to (−)-21 (FIG. 4); flash chromatography (EtOAc/hexanes, 50:50) afforded (−)-21 (20 mg, 64% yield); compound (−)-21 has physical and spectroscopic properties identical to literature values (Smith, A. B. III, et al., *J. Am. Chem. Soc.* (1994) 116:9947).

EXAMPLE 13

Preparation of Teoc-protected Amino Acid (+)-22

To a rt solution of (−)-31 (1.69 g, 7.94 mmol) in $CH_2Cl_2$ (30 mL) was added $Et_3N$ (4.02 g, 5.53 mL, 39.7 mmol). The mixture was stirred for 5 min, and then Teoc-O-succinimidyl (2.06 g, 7.94 mmol) was added in one portion. The reaction was stirred for 14 h, diluted with EtOAc (100 mL), washed with 2 N aqueous HCl (2×15 mL), saturated aqueous $NaHCO_3$ (15 mL) and brine (15 mL). The organic phase was separated, dried over anhydrous $MgSO_4$, and concentrated in vacuo. The resulting oil was purified by flash chromatography (EtOAc/hexanes, 20:80) to afford the corresponding Teoc-protected amino ester (2.5 g, 88% yield) as a oil: $[\alpha]_D^{23}$+38.7° (c 0.46, $CHCl_3$); IR (neat) 3425, 1714, 1503, 1444 $cm^{-1}$; $^1H$ NMR (500 MHz, $CDCl_3$) δ 5.71 (s, 1H), 4.88 (t, 1H, J=7.0 Hz), 4.09 (t, 2H, J=8.4 Hz), 3.70 (s, 3H), 2.99 (dd, 1H, J=6.9, 14.0 Hz), 2.40-2.36 (m, 2H), 1.69-1.63 (m, 1H), 1.60-1.51 (m, 1H), 1.64 (s, 3H), 1.58 (s, 3H), 0.98-0.93 (m, 2H), 0.88 (d, 3H, J=6.7 Hz), 0.75 (d, 3H, J=6.6 Hz), 0.02 (s, 9H); $^{13}C$ NMR (125 MHz, $CDCl_3$) δ 174.8, 154.4, 135.4, 117.8, 63.5, 62.4, 52.3, 43.8, 35.4, 25.9, 24.6, 23.8, 22.5, 17.8, 17.7, −1.5; high-resolution mass spectrum (CI, $NH_3$) m/z 358.2406 [(M+H)$^+$], calcd for $C_{18}H_{36}NO_4Si$ 358.2414. Anal. Calcd for $C_{18}H_{35}NO_4Si$: C, 60.46; H, 9.87. Found: C, 60.82; H, 9.72.

The solution of Teoc-protected amino ester (1.22 g, 3.42 mmol) in MeOH (20 mL) and 3 N aqueous NaOH (10 mL) was heated to reflux for 20 h. The mixture was cooled to rt and concentrated in vacuo; the resultant mixture was then acidified with saturated aqueous $NaHSO_4$ to pH 2 and then extracted with EtOAc (2×30 mL). The combined organic phases were washed with brine (15 mL), dried over anhydrous $MgSO_4$, concentrated in vacuo, and azeotroped with toluene (3×15 mL). This procedure gave (+)-22 (1.12 g, 96% yield) as a colorless oil that was used without further purification. Analytical sample: $[\alpha]_D^{23}$+21.00 (c 0.59, $CHCl_3$); IR ($CHCl_3$) 3421, 1707, 1505 $cm^{-1}$; $^1H$ NMR (500 MHz, $CDCl_3$) δ 5.61 (s, 1H), 4.95 (t, 1H, J=6.8 Hz), 4.15-4.09 (m, 2H), 3.04-2.98 (m, 1H), 2.46 (dd, 1H, J=7.4, 14.4 Hz), 2.37 (dd, 1H, J=4.8, 14.3 Hz), 1.78-1.70 (m, 1H), 1.67 (s, 3H), 1.66-1.60 (m, 1H), 1.58 (s, 3H), 1.02-0.95 (m, 2H), 0.91 (d, 3H, J=6.6 Hz), 0.83 (d, 3H, J=6.6 Hz), 0.03 (s, 9H); $^{13}C$ NMR (125 MHz, $CDCl_3$) δ 178.8, 154.6, 135.7, 117.5, 63.2, 62.6, 43.6, 35.3, 25.9, 24.7, 23.7, 22.7, 17.8, 17.6, −1.6; high-resolution mass spectrum (ES, Na$^+$) m/z 344.2251 [(M+H)$^+$], calcd for $C_{17}H_{34}NO_4Si$ 344.2257. Anal. Calcd for $C_{17}H_{33}NO_4Si$: C, 59.44; H, 9.68. Found: C, 59.22; H, 9.48.

EXAMPLE 14

Preparation of Resin Bound Teoc-protected Amino Acid 23

To a suspension of Wang resin (3.52 g, 2.92 mmol, 1.0 equiv), $PPh_3$ (0.84 g, 3.21 mmol, 1.1 equiv), and (+)-22 (1.10 g, 3.21 mmol, 1.1 equiv) in THF (55 mL) at 0° C. was added diethyl azodicarboxylate (0.51 mL, 0.56 g, 3.21 mmol, 1.1 equiv). The mixture was warmed to rt, shaken for 14 h, after which the resin was filtered, washed successively with THF (3×50 mL), $Et_2O$ (3×50 mL) and dried under high vacuum to a constant weight of 4.63 g. The resin was then re-subjected to the same reaction conditions to afford 23 (4.64 g): IR (KBr) 3429, 1717 $cm^{-1}$.

EXAMPLE 15

Preparation of Resin Bound Free Amino Acid 24

Typical Procedure for Teoc Deprotection With TBAF

To a suspension of resin bound Teoc-protected amino acid 23 (0.36 g, ca. 0.24 mmol, 1.0 equiv) in THF (8 mL) was added n-$Bu_4NF$ (1.18 mL, 1.18 mmol, 1.0 M in THF, 5.0 equiv). The reaction was shaken for 12 h, after which the resin was filtered, washed successively with THF/$H_2O$ (1:1, 3×20 mL), DMSO (3×15 mL), THF (3×20 mL), $Et_2O$ (3×20 mL) and dried under high vacuum to afford 24 (0.33 g): IR (KBr) 1722 $cm^{-1}$.

EXAMPLE 16

Preparation of Resin Bound Imine 25

Typical Procedure for Imine Formation With Hydrocinnamaldehyde

To a suspension of resin bound free amino acid 24 (60 mg, ca. 0.043 mmol, 1.0 equiv) in THF (3 mL) and $(MeO)_3CH$ (3 mL) was added hydrocinnamaldehyde (0.06 mL, 58 mg, 0.429 mmol, 10.0 equiv). The reaction was shaken for 12 h, after which the resin was filtered, washed successively with anhydrous THF (4×6 mL) under an argon atmosphere, and then dried under high vacuum. The resin was then re-subjected to the same reaction conditions to afford 25 which was taken immediately on to next step.

EXAMPLE 17

Synthesis of Mono-pyrrolinone (−)-26

Typical Procedure for the Cleavage of Substrate From the Resin

To a suspension of resin bound imine 25 (ca. 0.043 mmol, 1.0 equiv) in THF (5 mL) was added KHMDS (1.28 mL, 0.64 mmol, 0.5 M in toluene, 15.0 equiv). The reaction was shaken for 3 h, cooled to 0° C., and quenched by addition of 5% aqueous $NaHSO_4$ (3 mL). The resin was then filtered, washed successively with THF (2×10 mL), EtOAc (2×10 mL), $Et_2O$ (2×10 mL). The filtrate and the washes were combined, washed with saturated aqueous $NaHCO_3$ and brine (15 mL each), dried over anhydrous $MgSO_4$, and concentrated in vacuo. Flash chromatography (EtOAc/hexanes 20:80) afforded (−)-26 (7.9 mg, 62% yield) as a yellow solid which has physical and spectroscopic properties identical to literature values (Smith, A. B. III, et al., *J. Am. Chem. Soc.* (1994) 116: 9947).

EXAMPLE 18

Preparation of Resin Bound Teoc-protected Amino Aldehyde 27

A suspension of resin bound Teoc-protected amino acid 23 (1.74 g, ca. 1.14 mmol, 1.0 equiv) in $CH_2Cl_2$ (15 mL) was cooled to −78° C., and ozone bubbled into the mixture until a blue color persisted. The mixture was then stirred for another 20 min, and then the excess ozone purged with argon. To this suspension, $PPh_3$ (1.20 g, 4.55 mmol, 4.0 equiv) was added, and the reaction mixture was warmed to rt, shaken for 14 h, after which the resin was filtered, washed successively with $CH_2Cl_2$ (2×50 mL), THF (2×50 mL), $Et_2O$ (2×50 mL) and dried under high vacuum to afford 27 (1.62 g): IR (KBr) 3422, 1720 cm$^{-1}$.

EXAMPLE 19

Preparation of Resin Bound Mono-pyrrolinone 28

Typical Procedure for Pyrrolinone Ring Formation on Solid Support Using Amino Ester (−)-31

To a suspension of resin bound amino aldehyde 27 (1.62 g, ca. 1.08 mmol, 1.0 equiv) in THF (15 mL) and $(MeO)_3CH$ (15 mL) was added amino ester (−)-31 (0.58 g, 2.7 mmol, 2.5 equiv). The mixture was shaken for 12 h, after which the resin was filtered, washed successively with anhydrous THF (4×6 mL) under argon protection, and dried under high vacuum. The resin was then re-subjected to the same reaction conditions to afford the resin bound imine, which was immediately taken on to next step.

To a suspension of resin bound imine (ca. 1.08 mmol, 1.0 equiv) in THF (15 mL) was added KHMDS (21.6 mL, 10.8 mmol, 0.5 M in toluene, 10.0 equiv). The mixture was then shaken for 2 h, cooled to 0° C., and quenched by addition of saturated aqueous $NH_4Cl$ (5 mL). The resin was then filtered, washed successively with $H_2O$ (3×15 mL), $H_2O$/THF (1:1, 2×20 mL), THF (2×30 mL), $Et_2O$ (2×30 mL), dried under high vacuum to afford 28 (1.74 g).

EXAMPLE 20

Preparation of Resin Bound Monohydroxy Pyrrolinone 32

Typical Procedure for Pyrrolinone Ring Formation on Solid Support Using Amino Lactone (−)-7b To a suspension of resin bound amino aldehyde 27 (590 mg, ca. 0.39 mmol, 1.0 equiv) in THF (5 mL) and $(MeO)_3CH$ (5 mL) was added amino lactone (−)-7b (153 mg, 0.98 mmol, 2.5 equiv). The reaction was shaken for 12 h, after which the resin was filtered, washed successively with anhydrous THF (4×10 mL) under argon protection, and dried under high vacuum. The resin was then re-subjected to the same reaction conditions to afford the resin bound imine which was taken immediately on to next step.

To a 0° C. suspension of resin bound imine (ca. 0.39 mmol, 1.0 equiv) in THF (10 mL) was added a solution of KHMDS (6.28 mL, 3.14 mmol, 0.5 M in toluene, 8.0 equiv) and 18-c-6 (830 mg, 3.14 mmol, 8.0 equiv) in THF (6 mL) via cannula. The reaction was shaken at 0° C. for 2 h, at rt for 3 h, then cooled to 0° C., and quenched by addition of 5% aqueous $NaHSO_4$ (5 mL). The resin was then filtered, washed successively with $H_2O$ (3×15 mL), $H_2O$/THF (1:1, 2×30 mL), DMSO (3×15 mL), THF (2×30 mL), $Et_2O$ (2×30 mL), and dried under high vacuum to afford 32 (615 mg).

EXAMPLE 21

Preparation of Resin Bound Mono-pyrrolinone Aldehyde 33

Typical Procedure for Swern Oxidation on Solid Support

To a −70° C. solution of $(COCl)_2$ (0.44 mL, 0.88 mmol, 2.0 M in $CH_2Cl_2$, 2.5 equiv) in $CH_2Cl_2$ (4 mL) was added DMSO (0.14 mL, 137 mg, 1.75 mmol, 5.0 equiv). The resulting solution was stirred for 5 min, and then added to a suspension of resin bound monohydroxy pyrrolinone 32 (575 mg, ca. 0.35 mmol, 1.0 equiv) in $CH_2Cl_2$ (8 mL) via cotton wrapped cannula at −78° C. High vacuum was attached to the flask containing the resin to facilitate the addition process. The suspension was stirred for another 20 min at −78° C. and then DBU (0.39 mL, 399 mg, 2.62 mmol, 7.5 equiv) was added via syringe. The reaction was warmed to rt, stirred for 20 min, cooled back to 0° C., and quenched by addition of water (5 mL). The resin was then filtered, washed successively with $H_2O$ (3×15 mL), $H_2O$/THF (1:1, 2×30 mL), DMSO (3×15 mL), THF (2×30 mL), $Et_2O$ (2×30 mL), and dried under high vacuum to afford 33 (560 mg).

EXAMPLE 22

Preparation of Resin Bound Bis-pyrrolinone Amine

Typical Procedure for the Teoc Deprotection with CsF/TBAF

To a suspension of resin bound bis-pyrrolinone 34 (110 mg, ca. 0.06 mmol, 1.0 equiv) in anhydrous DMF (3.5 mL) was added CsF (46 mg, 0.31 mmol, 5.0 equiv). The reaction was shaken for 12 h, after which the resin was filtered, washed successively with THF/$H_2O$ (1:1, 3×10 mL), DMSO (3×10 mL), THF (3×10 mL), $Et_2O$ (3×10 mL) and dried under high vacuum.

To this resin was added THF (4 mL), followed by n-$Bu_4NF$ (0.31 mL, 0.31 mmol, 1.0 M in THF, 5.0 equiv). The reaction mixture was shaken for 4 h, after which the resin was filtered, washed successively with THF/$H_2O$ (1:1, 3×20 mL), DMSO (3×15 mL), THF (3×20 mL), $Et_2O$ (3×20 mL) and dried under high vacuum to afford bis-pyrrolinone amine (98 mg).

EXAMPLE 23

Synthesis of Tris-pyrrolinone (−)-35

Following the procedure described above for (−)-26 (Example 17), condensation of resin bound bispyrrolinone amine (91 mg, ca. 0.055 mmol) with hydrocinnamaldehyde followed by cyclization with KHMDS afforded (−)-35 (4.2 mg, 13.4%) as a yellow solid after flash chromatography (EtOAc/hexanes, 50:50): mp 90-95° C. dec; $[\alpha]_D^{23}$ −164.5° (c 0.4, $CHCl_3$); IR ($CHCl_3$) 3448, 1522, 1424 cm$^{-1}$; $^1$H NMR (500 MHz, $CDCl_3$) δ 8.25 (d, 1H, J=4.1 Hz), 8.16 (d, 1H, J=4.2

Hz), 7.58 (d, 1H, J=3.6 Hz), 7.38 (d, 1H, J=3.9 Hz), 7.23-7.19 (m, 2H), 7.16-7.08 (m, 4H), 5.26 (d, 1H, J=3.9 Hz), 4.95 (t, 11H, J=7.7 Hz), 3.47 (s, 2H), 2.31 (dd, 1H, J=7.6, 14.1 Hz), 2.22 (dd, 1H, J=7.0, 14.5 Hz), 1.82-1.75 (m, 2H), 1.66 (s, 3H), 1.58 (s, 3H), 1.65-1.38 (m, 7H), 0.82 (d, 3H, J=6.7 Hz), 0.81 (d, 3H, J=6.5 Hz), 0.80 (d, 3H, J=6.8 Hz), 0.79 (d, 3H, J=6.6 Hz), 0.72 (d, 3H, J=6.4 Hz), 0.70 (d, 3H, J=6.6 Hz); $^{13}$C NMR (125 MHz, CDCl$_3$) δ 203.43, 203.16, 202.27, 162.51, 161.64, 159.80, 140.83, 136.05, 128.46, 128.31, 125.83, 116.97, 112.45, 110.03, 108.65, 71.37, 68.68, 67.90, 47.98, 47.47, 44.78, 36.19, 28.46, 25.89, 24.83, 24.61, 24.52, 24.47, 24.36, 24.31, 23.81, 23.66, 23.40, 18.09; high-resolution mass spectrum (ES, Na$^+$) m/z 594.3681 [(M+Na)$^+$], calcd for C$_{36}$H$_{49}$N$_3$O$_3$Na 594.3672. Anal. Calcd for C$_{36}$H$_{49}$N$_3$O$_3$: C, 75.62; H, 8.64. Found: C, 75.42; H, 8.34.

EXAMPLE 24

Synthesis of Tetra-pyrrolinone (−)-37

Following the procedure described above for (−)-26, condensation of resin bound tris-pyrrolinone amine (282 mg, ca. 0.157 mmol) with hydrocinnamaldehyde followed by cyclization with KHMDS afforded (−)-37 (2.8 mg, 2.5%) as a yellow solid after flash chromatography (EtOAc/hexanes, 50:50), along with (−)-35 (2.6 mg, 2.9%); tetra-pyrrolinone (−)-37: mp 90-92° C. dec; [α]$_D^{23}$ −386.4° (c 0.3, CHCl$_3$); IR (CHCl$_3$) 3450, 1644, 1580, 1454 cm$^{-1}$; $^1$H NMR (500 MHz, CDCl$_3$) δ 8.28 (d, 1H, J=4.1 Hz), 8.19 (d, 1H, J=4.1 Hz), 8.18 (d, 1H, J=4.2 Hz), 7.59 (d, 11H, J=3.5 Hz), 7.45-7.42 (m, 2H), 7.24-7.21 (m, 2H), 7.19-7.13 (m, 4 H), 5.30 (d, 11H, J=4.0 Hz), 4.96 (t, 11H, J=7.6 Hz), 3.49 (s, 2H), 2.33 (dd, 11H, J=7.8, 14.6 Hz), 2.24 (dd, 1H, J=7.2, 14.6 Hz), 1.83-1.71 (m, 4H), 1.67 (s, 3H), 1.65-1.40 (m, 8H), 1.60 (s, 3H), 0.85-0.80 (series of doublet, 12H), 0.78 (d, 3H, J=6.7 Hz), 0.76 (d, 3H, J=6.2 Hz), 0.74 (d, 3H, J=6.6 Hz), 0.71 (d, 3H, J=6.6 Hz); $^{13}$C NMR (125 MHz, CDCl$_3$) δ 203.35, 203.18, 202.37, 202.20, 162.51, 161.66, 161.03, 159.88, 140.82, 136.04, 128.45, 128.30, 125.82, 116.91, 112.26, 109.74, 108.68, 108.29, 71.38, 68.76, 68.47, 67.89, 48.03, 47.65, 47.56, 44.76, 36.17, 28.47, 25.88, 24.80, 24.64, 24.61, 24.46, 24.42, 24.41, 24.33, 24.31, 23.83, 23.61, 23.56, 23.52, 18.09; high-resolution mass spectrum (ES, Na$^+$) m/z 709.4678 [(M+H)$^+$], calcd for C$_{44}$H$_{61}$N$_4$O$_4$ 709.4693.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true scope and spirit of the invention.

We claim

1. A solid-phase process for preparing an optical isomer of a polypyrrolinone comprising the steps:
(a) linking an optical isomer of carboxylic acid that contains a latent aldehyde to a solid support wherein the latent aldehyde is converted to an aldehyde (41);

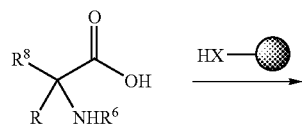

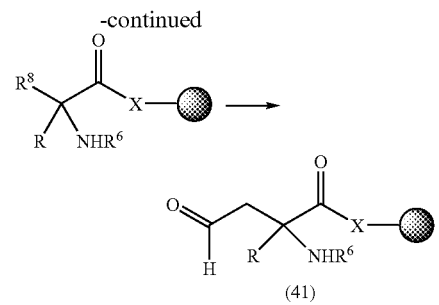

wherein:

R$^6$ is an amino protecting group,

R$^8$ is 3-methyl-1-but-2-enyl, 2,2-dimethoxyethyl, 2-hydroxyethyl, and

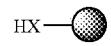

is para-hydroxy benzyl alcohol resin;

(b) reacting an α-amino-α-substituted-1,4-dioxo compound (41), optionally with an alkoxycarbonyl protecting group, with an optical isomer of 2-substituted-2-aminovalerolactone (7), trimethylorthoformate, optionally in the presence of a solvent, to produce imine (40)

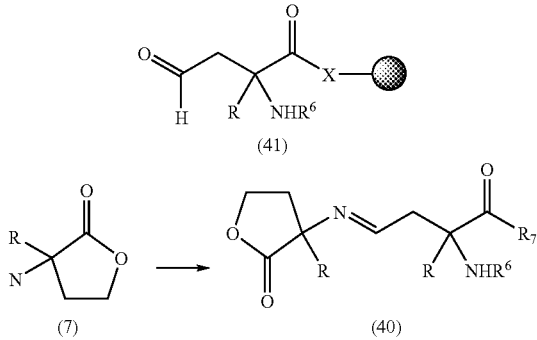

wherein:

R$^6$ is an amino protecting group;

R$^7$ is a carboxyl linked to a solid support;

(c) cyclizing (40) by forming metalloimine carbanion with base, optionally in the presence of a crown ether, to form a pyrrolinone (41)

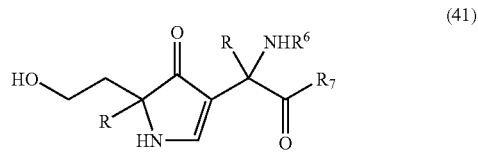

(d) oxidizing the —CH$_2$CH$_2$OH group to the corresponding aldehyde;

(e) repeating steps (b)-(d) m times to produce polypyrrolinone (42)

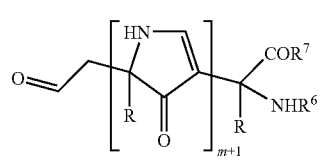
(42)

(f) terminating the synthesis using a substituted α amino acid ester in place of the valerolactone (7) in step (b) to yield (43)

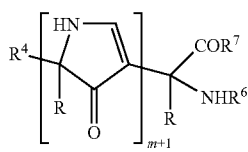
(43)

(g) Cleaving the polypyrrolinone from the resin by removing the protecting group $R^6$ in (43), and exposing the resulted free $NH_2$ moiety to a plurality of treatments with an aldehyde, trimethylorthoformate, optionally in the presence of a solvent, to produce the corresponding imine; and, (h) cyclizing the imine by forming the metalloimine carbanion with base, optionally in the presence of a crown ether, to produce the (i) the polypyrrolinone having the formula (38)

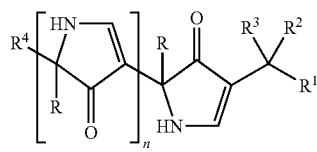
(38)

wherein:

R is independently selected from a group consisting of a straight $C_1$-$C_6$ alkyl, a branched $C_3$-$C_7$ alkyl, $C_3$-$C_7$ cycloalkyl, a straight $C_1$-$C_6$ alkenyl, a branched $C_3$-$C_7$ alkenyl, $C_1$-$C_4$ hydroxyalkyl, $C_1$-$C_4$ thioalkyl, $C_1$-$C_4$ methylthioalkyl, —$(CH_2)_oN(R^5)_2$, —$(CH_2)_oCO_2H$, —$(CH_2)_oCON(R^5)_2$, heteroaryl, phenyl optionally substituted with one to three hydroxyl, $C_1$-$C_8$ alkoxy, halo, nitro, or cyano groups, and benzyl optionally substituted with one to three hydroxyl, $C_1$-$C_8$ alkoxy, halo, nitro or cyano groups;

$R^1$ is hydrogen, hydroxyl, $C_1$-$C_8$ alkoxy, amino or alkoxycarbonyl-protected amino;

$R^2$ is R, carboxyl, a carbonyl linked to a solid support or alkoxycarbonyl;

$R^3$ is R or hydrogen;

$R^4$ is R or (46)

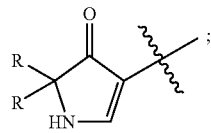
(46)

$R^5$ is hydrogen or $C_1$-$C_8$ alkyl;

n is 0 to 3;

o is 1 to 4;

wherein the stereochemical configuration, R or S, is preserved at each chiral center of the starting material through the ultimate product.

2. A solid-phase process for preparing an optical isomer of a polypyrrolinone comprising the steps:

(a) linking an optical isomer of carboxylic acid that contains a latent aldehyde to a solid support wherein the latent aldehyde is converted to an aldehyde (41);

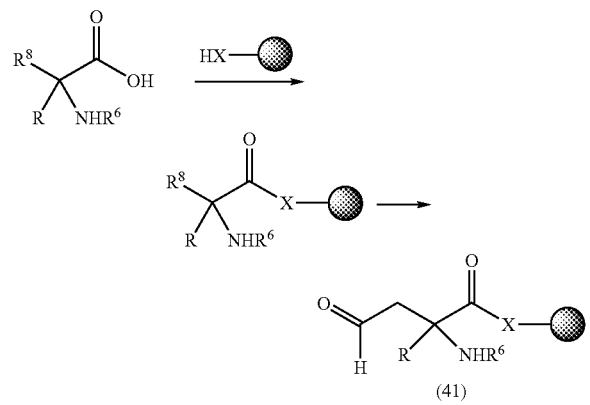
(41)

wherein:

$R^6$ is an amino protecting group, $R^8$ is 3-methyl-1-but-2-enyl, 2,2-dimethoxyethyl, 2-hydroxyethyl, and

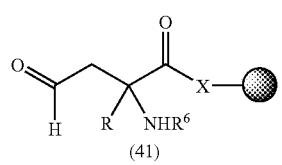

is a Wang resin;

(b) reacting an α-amino-α-substituted-1,4-dioxo compound (41), optionally with an alkoxycarbonyl protecting group, with an optical isomer of 2-substituted-2-aminovalerolactone (7), trimethylorthoformate, optionally in the presence of a solvent, to produce imine (40)

-continued

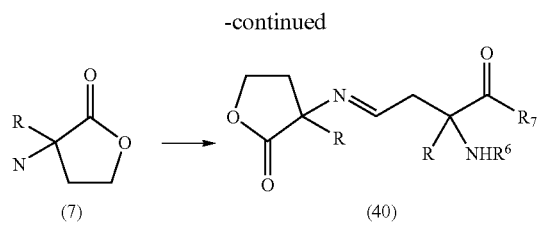

wherein:
$R^6$ is an amino protecting group;
$R^7$ is a carboxyl linked to a solid support;

(c) cyclizing (40) by forming metalloimine carbanion with base, optionally in the presence of a crown ether, to form a pyrrolinone (41)

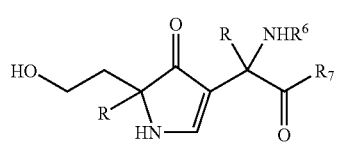

(d) oxidizing the —$CH_2CH_2OH$ group to the corresponding aldehyde;
(e) repeating steps (b)-(d) m times to produce polypyrrolinone (42)

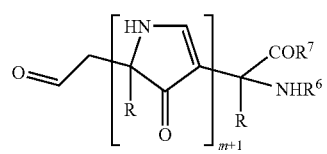

(f) terminating the synthesis using a substituted α amino acid ester in place of the valerolactone (7) in step (b) to yield (43)

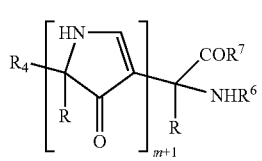

(g) Cleaving the polypyrrolinone from the resin by removing the protecting group $R^6$ in (43), and exposing the resulted free $NH_2$ moiety to a plurality of treatments with an aldehyde, trimethylorthoformate, optionally in the presence of a solvent, to produce the corresponding imine; and,
(h) cyclizing the imine by forming the metalloimine carbanion with base, optionally in the presence of a crown ether, to produce the
(i) the polypyrrolinone having the formula (38)

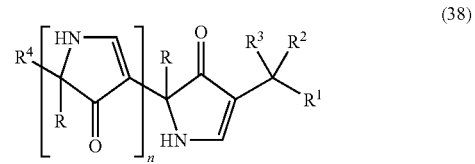

wherein:
R is independently selected from a group consisting of a straight $C_1$-$C_6$ alkyl, a branched $C_3$-$C_7$ alkyl, $C_3$-$C_7$ cycloalkyl, a straight $C_1$-$C_6$ alkenyl, a branched $C_3$-$C_7$ alkenyl, $C_1$-$C_4$ hydroxyalkyl, $C_1$-$C_4$ thioalkyl, $C_1$-$C_4$ methylthioalkyl, —$(CH_2)_oN(R^5)_2$, —$(CH_2)_oCO_2H$, —$(CH_2)_oCON(R^5)_2$, heteroaryl, phenyl optionally substituted with one to three hydroxyl, $C_1$-$C_8$ alkoxy, halo, nitro, or cyano groups, and benzyl optionally substituted with one to three hydroxyl, $C_1$-$C_8$ alkoxy, halo, nitro or cyano groups;
$R^1$ is hydrogen, hydroxyl, $C_1$-$C_8$ alkoxy, amino or alkoxycarbonyl-protected amino;
$R^2$ is R, carboxyl, a carbonyl linked to a solid support or alkoxycarbonyl;
$R^3$ is R or hydrogen;
$R^4$ is R or (46)

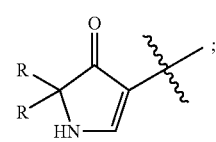

$R^5$ is hydrogen or $C_1$-$C_8$ alkyl;
n is 0 to 3;
o is 1 to 4;
wherein the stereochemical configuration, R or S, is preserved at each chiral center of the starting material through the ultimate product.

3. A solid-phase process for preparing an optical isomer of a polypyrrolinone comprising the steps:
(a) linking an optical isomer of carboxylic acid that contains a latent aldehyde to a solid support wherein the latent aldehyde is converted to an aldehyde (41);

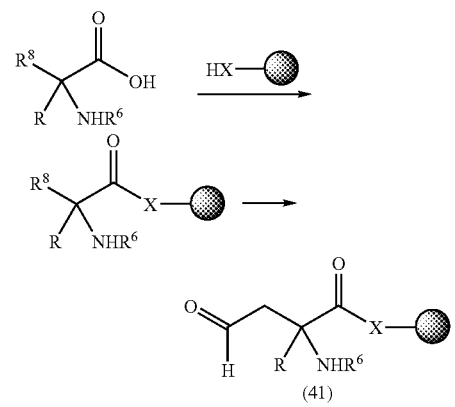

wherein:
$R^6$ is an amino protecting group, $R^8$ is 3-methyl-1-but-2-enyl, 2,2-dimethoxyethyl, 2-hydroxyethyl, and

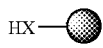

is para-hydroxy benzyl alcohol resin;

(b) reacting an α-amino-α-substituted-1,4-dioxo compound (41), optionally with an alkoxycarbonyl protecting group, with an optical isomer of 2-substituted-2-aminovalerolactone (7), trimethylorthoformate, optionally in the presence of a solvent, to produce imine (40)

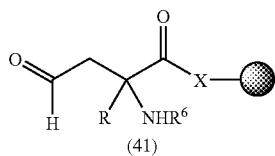

(41)

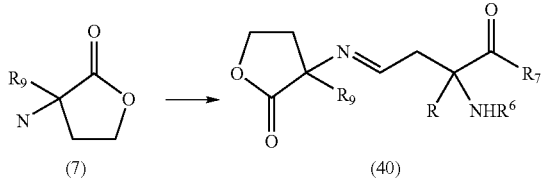

(7)  (40)

wherein:
$R^6$ is an amino protecting group;
$R^7$ is a carboxyl linked to a solid support;
$R^9$ corresponds to the side chain of an individual amino acid in a polypeptide;

(c) cyclizing (40) by forming metalloimine carbanion with base, optionally in the presence of a crown ether, to form a pyrrolinone (41)

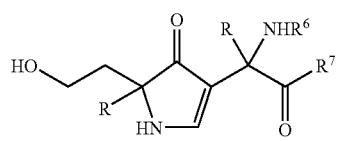

(41)

(d) oxidizing the —CH$_2$CH$_2$OH group to the corresponding aldehyde;
(e) repeating steps (b)-(d) m times to produce polypyrrolinone (42)

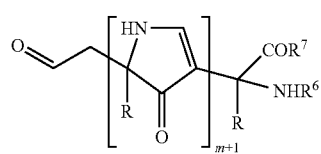

(42)

(f) terminating the synthesis using a substituted α amino acid ester in place of the valerolactone (7) in step (b) to yield (43)

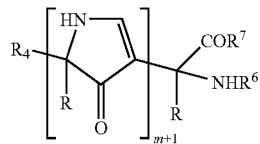

(43)

(g) Cleaving the polypyrrolinone from the resin by removing the protecting group $R^6$ in (43), and exposing the resulted free NH$_2$ moiety to a plurality of treatments with an aldehyde, trimethylorthoformate, optionally in the presence of a solvent, to produce the corresponding imine; and,
(h) cyclizing the imine by forming the metalloimine carbanion with base, optionally in the presence of a crown ether, to produce the
(i) the polypyrrolinone having the formula (38)

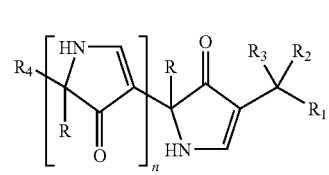

(38)

wherein:
R is independently selected from a group consisting of a straight $C_1$-$C_6$ alkyl, a branched $C_3$-$C_7$ alkyl, $C_3$-$C_7$ cycloalkyl, a straight $C_1$-$C_6$ alkenyl, a branched $C_3$-$C_7$ alkenyl, $C_1$-$C_4$ hydroxyalkyl, $C_1$-$C_4$ thioalkyl, $C_1$-$C_4$ methylthioalkyl, —(CH$_2$)$_o$N(R$^5$)$_2$, —(CH$_2$)$_o$CO$_2$H, —(CH$_2$)$_o$CON(R$^5$)$_2$, heteroaryl, phenyl optionally substituted with one to three hydroxyl, $C_1$-$C_8$ alkoxy, halo, nitro, or cyano groups, and benzyl optionally substituted with one to three hydroxyl, $C_1$-$C_8$ alkoxy, halo, nitro or cyano groups;
$R^1$ is hydrogen, hydroxyl, $C_1$-$C_8$ alkoxy, amino or alkoxycarbonyl-protected amino;
$R^2$ is R, carboxyl, a carbonyl linked to a solid support or alkoxycarbonyl;
$R^3$ is R or hydrogen;
$R^4$ is R or (46)

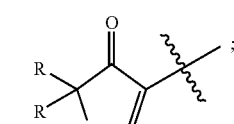

(46)

$R^5$ is hydrogen or $C_1$-$C_8$ alkyl;
n is 0 to 3;
o is 1 to 4;
wherein the stereochemical configuration, R or S, is preserved at each chiral center of the starting material through the ultimate product.

4. A process according to claim 1 wherein the oxidant in step (d) is oxalyl chloride, a tertiary amine and dimethylsulfoxide (DMSO).

5. A process according to claim 1 wherein the tertiary amine is diazabicycloundecene or di-iso-propylethyl amine.

6. A process according to claim 1 wherein the crown ether in step (c) is 18-crown-6.

7. A process according to claim 1 wherein the base in step (c) is potassium hexamethyldisilazane.

8. A process according to claim 1 wherein $R^6$ is a trialkylsilylethoxycarbonyl group.

9. A process according to claim 1 wherein the aldehyde in step (g) is a 3-phenylpropionaldehyde (49) derivative optionally substituted at the 3-position with one or two $R^3$ substituents

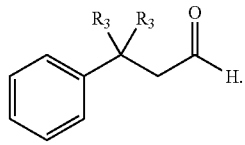

(49)

10. A process according to claim 1 wherein the aldehyde in step (g) is 3-phenylpropionaldehyde.

11. A process according to claim 3 wherein the para-hydroxy benzyl alcohol resin is a Wang resin.

* * * * *